(12) United States Patent
Morrison et al.

(10) Patent No.: US 10,946,151 B2
(45) Date of Patent: Mar. 16, 2021

(54) ULTRASONIC MEASUREMENTS FOR MONITORING PATIENTS USING RESPIRATORY THERAPY DELIVERY DEVICES

(71) Applicant: KONINKLIJKE PHILIPS N.V., Eindhoven (NL)

(72) Inventors: Mark Steven Morrison, Basking Ridge, NJ (US); Dirk Ernest Von Hollen, Clark, NJ (US)

(73) Assignee: Koninklijke Philips N.V., Eindhoven (NL)

(*) Notice: Subject to any disclaimer, the term of this patent is extended or adjusted under 35 U.S.C. 154(b) by 958 days.

(21) Appl. No.: 14/903,712

(22) PCT Filed: Jul. 2, 2014

(86) PCT No.: PCT/IB2014/062794
§ 371 (c)(1),
(2) Date: Jan. 8, 2016

(87) PCT Pub. No.: WO2015/004576
PCT Pub. Date: Jan. 15, 2015

(65) Prior Publication Data
US 2016/0166790 A1 Jun. 16, 2016

Related U.S. Application Data

(60) Provisional application No. 61/844,038, filed on Jul. 9, 2013.

(51) Int. Cl.
*A61M 16/00* (2006.01)
*A61M 15/00* (2006.01)
*A61M 16/16* (2006.01)

(52) U.S. Cl.
CPC ........ *A61M 16/0069* (2014.02); *A61M 15/00* (2013.01); *A61M 15/001* (2014.02);
(Continued)

(58) Field of Classification Search
CPC ........ A61M 11/00; A61M 11/001–008; A61M 13/00; A61M 15/00–011;
(Continued)

(56) References Cited

U.S. PATENT DOCUMENTS 5,468,961 A * 11/1995 Gradon ................. A61M 16/16
250/343
5,794,612 A 8/1998 Wachter
(Continued)

FOREIGN PATENT DOCUMENTS

| CN | 202289114 U | 7/2012 |
|----|-------------|--------|
| JP | H05123401 A | 5/1993 |

*Primary Examiner* — Jan Christopher L Merene
*Assistant Examiner* — Ned T Heffner
(74) *Attorney, Agent, or Firm* — Daniel H. Brean

(57) ABSTRACT

Systems and methods for delivering therapy and/or medicament to a subject use one or more sensors to generate signals that represent characteristics of ultrasonic energy emitted during the use of respiratory medicament delivery devices. Parameters based on these signals indicate energy amplitude in one or more frequency ranges. Such parameters can be used to characterize the emitted ultrasonic energy and control and/or monitor device operation and/or patient adherence.

9 Claims, 19 Drawing Sheets

(52) U.S. Cl.
CPC ...... *A61M 15/009* (2013.01); *A61M 15/0085* (2013.01); *A61M 16/0003* (2014.02); *A61M 16/161* (2014.02); A61M 2205/0294 (2013.01); A61M 2205/3303 (2013.01); A61M 2205/3368 (2013.01); A61M 2205/3375 (2013.01); A61M 2205/50 (2013.01); A61M 2230/40 (2013.01)

(58) Field of Classification Search
CPC ....... A61M 15/002–08; A61M 15/0065–0078; A61M 15/0085; A61M 15/009; A61M 15/06; A61M 15/08; A61M 15/085
See application file for complete search history.

(56) References Cited

U.S. PATENT DOCUMENTS

| | | | |
|---|---|---|---|
| 6,192,876 B1* | 2/2001 | Denyer | A61B 5/087 128/204.18 |
| 8,701,659 B2 | 4/2014 | Cosic | |
| 8,960,189 B2 | 2/2015 | Morrison | |
| 9,289,569 B2 | 3/2016 | Cardelius et al. | |
| 9,352,107 B2 | 5/2016 | Von Hollen et al. | |
| 10,675,422 B2* | 6/2020 | Morrison | A61M 11/005 |
| 2004/0050860 A1* | 3/2004 | Crowder | A61M 15/0045 222/1 |
| 2011/0226237 A1 | 9/2011 | Morrison | |
| 2012/0312302 A1* | 12/2012 | Cardelius | A61M 16/024 128/203.14 |

* cited by examiner

ULTRASONIC MEASUREMENTS FOR MONITORING PATIENTS USING RESPIRATORY THERAPY DELIVERY DEVICES

CROSS-REFERENCE TO RELATED APPLICATIONS

This patent application claims the priority benefit under 35 U.S.C. § 371 of international patent application no. PCT/IB2014/062794, filed Jul. 2, 2014, which claims the priority benefit under 35 U.S.C. § 119(e) of U.S. Provisional Application No. 61/844,038 filed on Jul. 9, 2013, the contents of which are herein incorporated by reference.

BACKGROUND

1. Field

The present disclosure pertains to systems and methods that measure ultrasonic energy emitted during the use of respiratory therapy delivery devices, and, in particular, to control and/or monitor device operation and/or patient adherence based thereon.

2. Description of the Related Art

Respiratory therapy delivery devices include respiratory drug delivery devices. Respiratory therapy delivery devices are used to treat many types of patients. As used herein, respiratory drug delivery devices may be referred to as respiratory medicament delivery devices. Some types of respiratory drug delivery devices, for example nebulizers, may include components that mechanically move at frequencies in the ultrasonic range. Device performance may depend on controlling such components with sufficient accuracy and efficacy. Positive treatment outcomes may depend on many factors, including patient adherence.

SUMMARY

Accordingly, one or more embodiments provide a system configured to provide respiratory therapy to a subject. The system comprises a respiratory therapy delivery device, a sensor, and one or more processors configured to execute computer program modules, the computer program modules. The respiratory therapy delivery device is configured to deliver breathable gas to an airway of a subject. The respiratory therapy delivery device may emit ultrasonic energy during operation. The sensor is configured to generate output signals representing one or more characteristics of the ultrasonic energy emitted by one or both of the respiratory therapy delivery device and/or the airway of the subject. The computer program modules comprise a parameter determination module, a characterization module, and/or other modules. The parameter determination module is configured to determine, based on the generated output signals, a first parameter that indicates energy amplitude of emitted ultrasonic energy. The characterization module is configured to determine a characterization of the emitted ultrasonic energy. The characterization may be based on the first parameter.

It is yet another aspect of one or more embodiments to provide a method of providing respiratory therapy to a subject. The method comprises delivering, by a respiratory therapy delivery device, breathable gas to an airway of a subject; generating, by a sensor, output signals representing one or more characteristics of the ultrasonic energy emitted by one or both of the respiratory therapy delivery device and/or the airway of a subject; determining a first parameter that indicates energy amplitude of the emitted ultrasonic energy; and determining a characterization of the emitted ultrasonic energy based on the first parameter.

It is yet another aspect of one or more embodiments to provide a system configured to provide respiratory therapy to a subject. The system comprises means for delivering breathable gas to an airway of a subject; means for generating output signals representing one or more characteristics of the ultrasonic energy emitted by one or both of the means for delivering and/or emitted from the airway of the subject; means for determining a first parameter that indicates energy amplitude of the emitted ultrasonic energy based on the generated output signals; and means for determining a characterization of the emitted ultrasonic energy, wherein the characterization is based on the first parameter.

These and other aspects, features, and characteristics of the present disclosure, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of any limits.

DETAILED DESCRIPTION OF EXEMPLARY EMBODIMENTS

Figure 1:
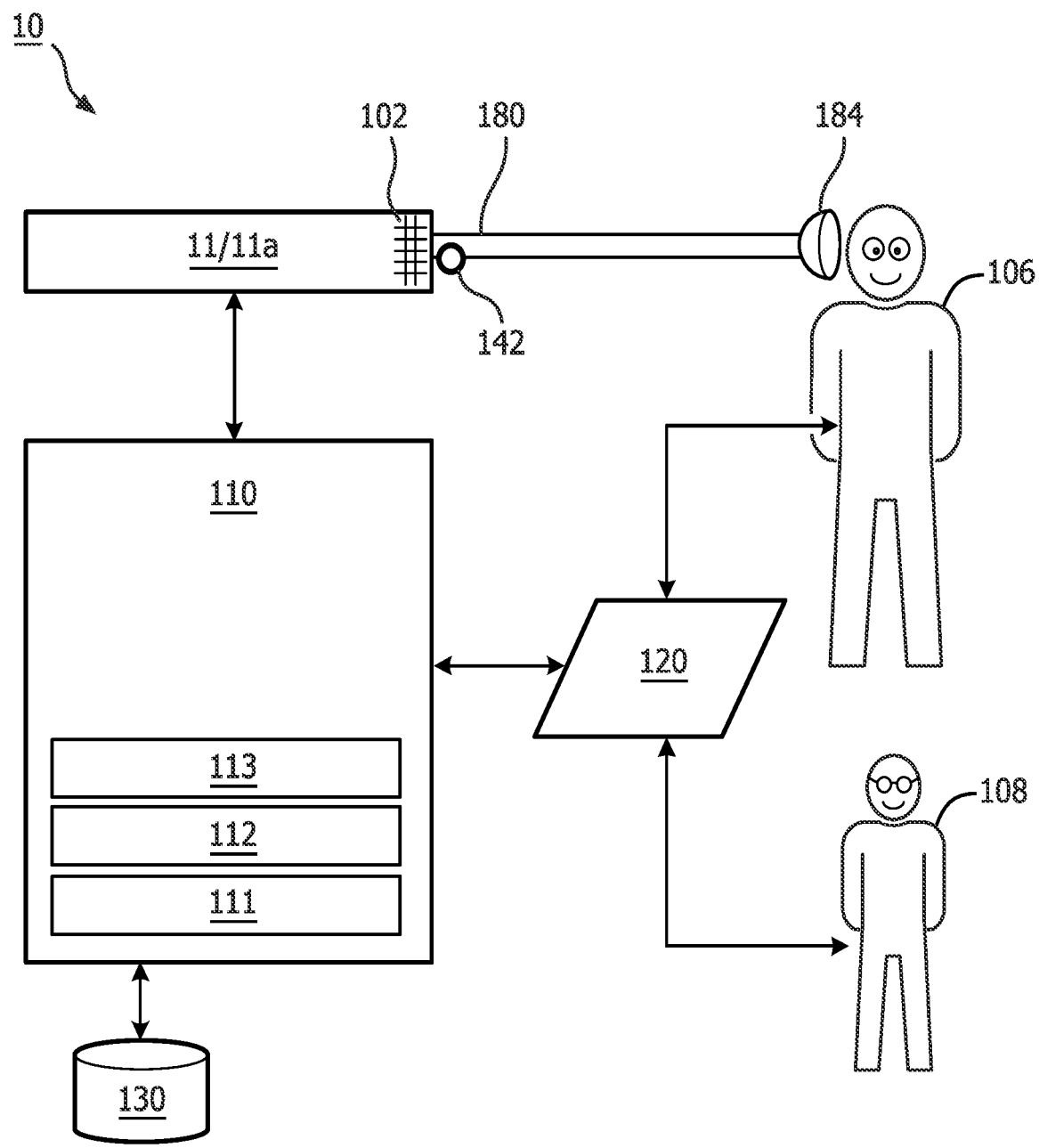
FIGS. 1, 12-13, and 18 schematically illustrate systems configured to deliver respiratory therapy to a subject.

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

FIG. 1 schematically illustrates a system 10 configured to provide respiratory therapy to a subject 106, including but not limited to respiratory drug delivery, devices that provide oxygen, (positive) airway pressure devices, humidification systems, devices that aid patients with sleeping, devices that provide ventilation and/or other types of respiratory therapy. In some implementations, system 10 may include a respiratory therapy delivery device 11a. The delivered respiratory therapy may, by way of non-limiting example, include delivery of medicament. For example, system 10 may include a respiratory medicament delivery device 11. System 10 may include one or more of a piezoelectric element 102, one or more sensors 142, one or more processors 110, a parameter determination module 111, a control module 112, a characterization module 113, an electronic storage 130, a user interface 120, and/or other components and/or computer program modules.

As used herein, respiratory therapy delivery devices and respiratory medicament delivery devices may be jointly referred to as respiratory devices.

A respiratory device may include one or more of a jet nebulizer, a mesh nebulizer, an ultrasonic wave nebulizer, a nebulizer, an aerosol generator, a metered-dose inhaler, a dry-powder inhaler, an inhaler, and/or another device configured to deliver medicament to a subject through, at least in part, respiration of the subject. In some implementations, a respiratory device may include one or more features of any of these devices. For example, respiratory medicament delivery device 11 may be configured to combine breathable gas, e.g. air, and medicament, e.g. liquid and/or aerosolized drugs, for delivery to the airway of subject 106. In some implementations, the respiratory device may be operated by a care provider 108, e.g. a medical professional. In some implementations, the respiratory device may include a conduit 180 to guide gas and/or medicament to subject 106 and/or a mouthpiece or mask 184 to deliver gas and/or medicament from conduit 180 to the airway of subject 106.

Respiratory therapy delivery device 11a and/or respiratory medicament delivery device 11 may emit energy during operation, including, but not limited to, ultrasonic energy. A respiratory device may be configured such that a constituent component thereof displaces air and/or gas through mechanical movement at an ultrasonic frequency. Such displacement may be indirect, e.g. when a moving component is coupled to another component which transfers energy to air and/or gas. In some implementations, a respiratory device may emit energy in a frequency range between about 18 kHz and about 200 kHz, and/or any sub-range thereof. In some implementations, measurements of the ultrasonic energy emitted by respiratory medicament delivery device 11 may change and/or alter based on environmental and/or ambient conditions, including but not limited to temperature, humidity, and/or chemical composition of a gas.

In some implementations, subject 106 (and/or the airway of subject 106) may emit energy in an ultrasonic frequency range (or borderline ultrasonic frequency range), for example, and without limitation, between about 15 kHz and about 75 kHz. The specific frequency range may depend on the type of respiratory device that is used, patient-specific conditions, and/or a range specific to a particular medical condition. In some implementations, subject 106 may emit energy during one or both of inhalation and/or exhalation. In some implementations, subjects suffering from one or more particular medical conditions, including but not limited to chronic obstructive pulmonary disease (COPD), asthma, and the common cold, may emit ultrasonic energy in one or more corresponding particular frequency ranges. Measurements of ultrasonic energy emitted by subject 106 may be used as diagnostic tools for one or more particular medical conditions, assessments of patient status and/or health, and/or other characteristic parameters related to respiration. In some implementations, measurements of ultrasonic energy emitted by subject 106 may be used to control breath-activation (interchangeably referred to as breath-actuation) of a respiratory device. In some implementations, measurements of ultrasonic energy emitted by subject 106 may be used to determine information related to patient adherence.

A respiratory device may include a mesh nebulizer and/or components/features thereof. In some implementations, a respiratory device may include an ultrasonic wave nebulizer and/or components/features thereof. The respiratory device may include a piezoelectric element 102 to provide mechanical vibration and thus displacement of a medium, e.g. liquid or air. Even nebulizers filled with liquid may include moving components that transfer ultrasonic energy to air and/or gas. In some implementations, one or more other surfaces in direct contact with air and/or gas may move as a result of the motion of, e.g., a piezoelectric element. Any vibrating surface may emit ultrasonic energy. For example, the backside of piezoelectric element 102 may contact (and/or be coupled with) air and/or gas. In some implementations, piezoelectric element 102 is coupled with a mesh (e.g. in a mesh nebulizer) having a side that is directly (or indirectly) in contact with air and/or gas. In some implementations, a static mesh may be placed at some harmonic distance from a vibrating piezoelectric element.

Piezoelectric elements may achieve maximum displacement at one or more particular frequencies, which may be referred to as resonant frequencies. Maximum displacement may be targeted as a preferred mode of operation, at least during medicament delivery. Operating conditions and/or maximum displacement may change over time, e.g. depending on the amount of available medicament within the device, the loading, drift of an oscillator used with/within the device, wear and tear of the device, ambient operating conditions such as temperature, humidity, atmospheric pressure, air density, and/or other factors that may change over time. Operating conditions and/or maximum displacement may differ between individual devices, e.g. based on construction, assembly, and/or other device-specific conditions. The particular operating condition having maximum displacement may be assumed to coincide, or at least be close to, the operating condition in which a maximum amount of ultrasonic energy is emitted. As used herein, the term "maximum" may refer to a local maximum in a specific range of operation.

By virtue of this disclosure, operating conditions for respiratory devices may be controlled and/or adjusted to track changes in (maximum) displacement (e.g. of a piezoelectric element), operating conditions, target frequencies similar and/or close to resonant frequencies, and/or monitor device usage (e.g. as indicative of patient adherence), patient-specific respiratory parameters, and/or other changes/conditions/parameters. Control and/or adjustment may be based on measurements of ultrasonic energy emitted by one or both of a respiratory device and/or the airway of subject 106. In some implementations, adjustments may be made in real-time or near-real-time. In some implementations, adjustments may be made automatically, autonomously, and/or without (manual) user intervention. In some implementations, a respiratory device may include an electronic oscillator or similar device/component to control the driving frequency of a piezoelectric element and/or other component configured for intentional displacement of, e.g., a medium.

Figure 9:
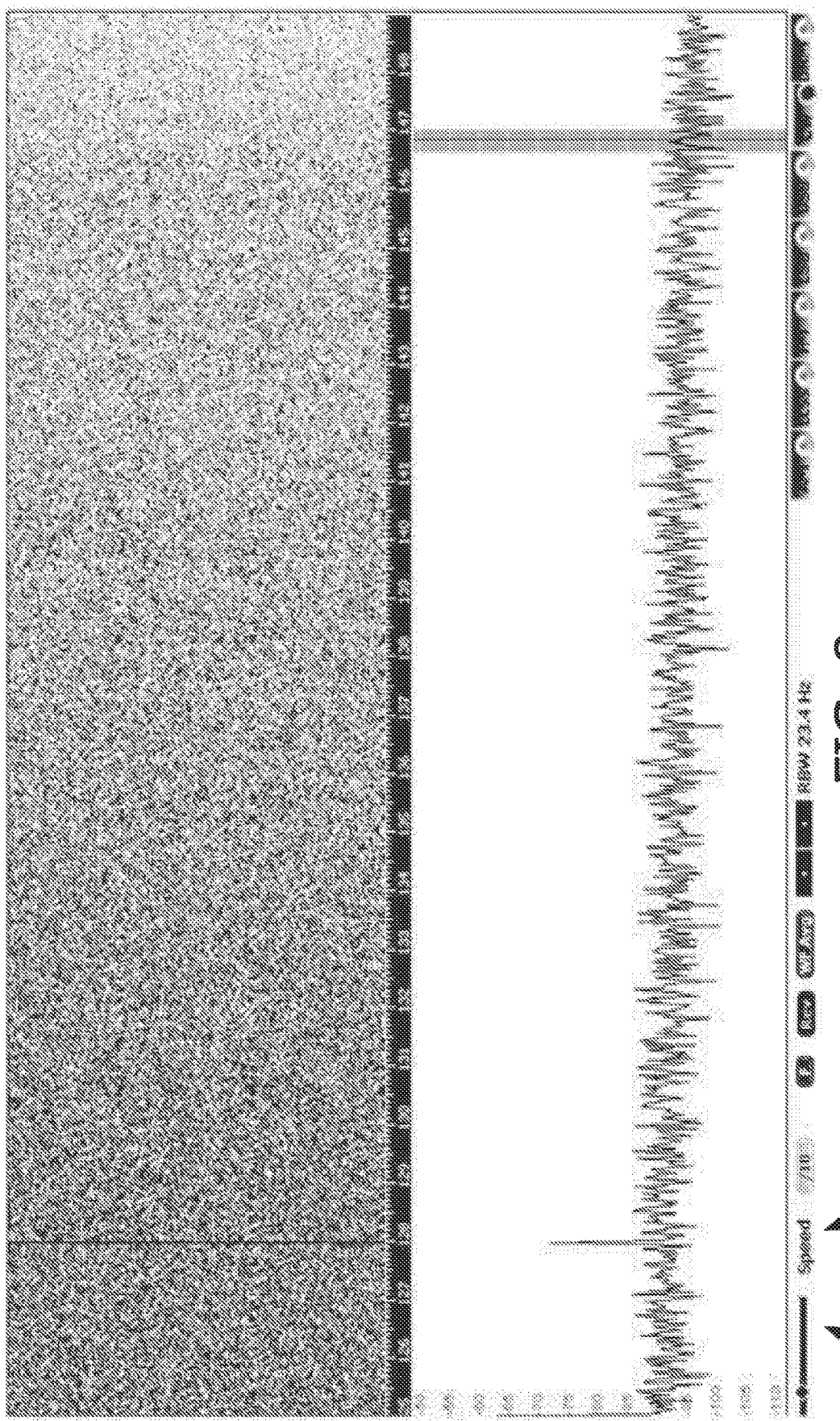

By way of illustration, FIG. 9 illustrates a graph 900 for energy emitted during the operation of a mesh nebulizer that includes a piezoelectric element. Graph 900 includes a waterfall display in the top half, and a magnitude (of energy amplitude) in the bottom half. The waterfall display shows time on the vertical axis and measured frequency (in kHz) on the horizontal axis. As depicted in FIG. 9, graph 900 includes a narrow peak magnitude near a frequency of 128 kHz, which is the operating frequency for the piezoelectric element in the mesh nebulizer. Referring to FIG. 1, energy may be measured using one or more sensors 142. As used herein, the term "magnitude" may be used to refer to the energy amplitude at a particular frequency and/or within a particular range of frequencies.

One or more sensors 142 of system 10 in FIG. 1 are configured to generate output signals representing one or more characteristics of ultrasonic energy emitted by one or more of respiratory therapy delivery device 11a, respiratory medicament delivery device 11, and/or (the airway of) subject 106. In some implementations, sensor 142 may include a microphone (interchangeably referred to as microphone 142). For example, sensor 142 may include a microphone constructed as a micro-electro-mechanical system (MEMS) or nano-electro-mechanical system (NEMS). As used herein, the term "MEMS" may be used to refer to either MEMS or NEMS. As used in this disclosure, the term "microphone" may be used to refer to a MEMS microphone, and may be used for audible and/or ultrasonic frequencies/sounds from any source or sources that emit such energy, including subject 106.

The one or more sensors 142 may include an accelerometer, positional sensor, movement sensor, light sensor, infrared (IR) sensor, electromagnetic sensor, electrode, tilt meter, (video) camera, and/or other sensors. The illustration of sensor 142 including one member in FIG. 1 is not intended to be limiting. In some embodiments, system 10 may use multiple sensors. The illustration of the location of sensor 142 as depicted in FIG. 1 is not intended to be limiting. An individual sensor 142 may be located at or near (a body part of) subject 106, embedded and/or integrated in a respiratory device, and/or at other locations. Resulting output signals or conveyed information from one or more sensors 142 may be transmitted to processor 110, user interface 120, electronic storage 130, and/or other components of system 10. Transmission may be wired and/or wireless.

The one or more sensors 142 may be configured to generate output signals in an ongoing manner, e.g. before, during, and/or after delivery of medicament. This may include generating signals intermittently, periodically (e.g. at a sampling rate), continuously, continually, at varying intervals, and/or in other ways that are ongoing. The sampling rate may be about 10−9 second, about 10−8 second, about 10−7 second, 10−6 second, 10−5 second, 10−4 second, 10−3 second, 0.01 second, 0.1 second, 1 second, about 10 seconds, about 1 minute, and/or other sampling rates. It is noted that multiple individual sensors 142 may operate using different sampling rates, as appropriate for the particular output signals and/or (frequencies related to particular) parameters and/or characteristics derived therefrom. For example, in some embodiments, the generated output signals may be considered as a vector of output signals, such that a vector includes multiple samples of information conveyed related to one or more parameters and/or characteristics. A particular parameter or characteristic determined in an ongoing manner from a vector of output signals may be considered as a vector of that particular parameter or characteristic.

In some implementations, sensor 142 may include a MEMS microphone configured and/or arranged to measure ultrasonic energy transferred from any flat and/or curved surface within a respiratory device, any exterior surface thereof, and/or (the airway of) subject 106. For example, (ultrasonic) energy emitted by subjects may be different between inhalation and exhalation. During inhalation, subjects may emit ultrasonic energy having a frequency of about 20 kHz. During exhalation, subjects typically emit ultrasonic energy having a frequency lower than 20 kHz, or no discernible emission of ultrasonic energy. This distinction between inhalation and exhalation may be used by the systems and methods described herein.

Figure 15:
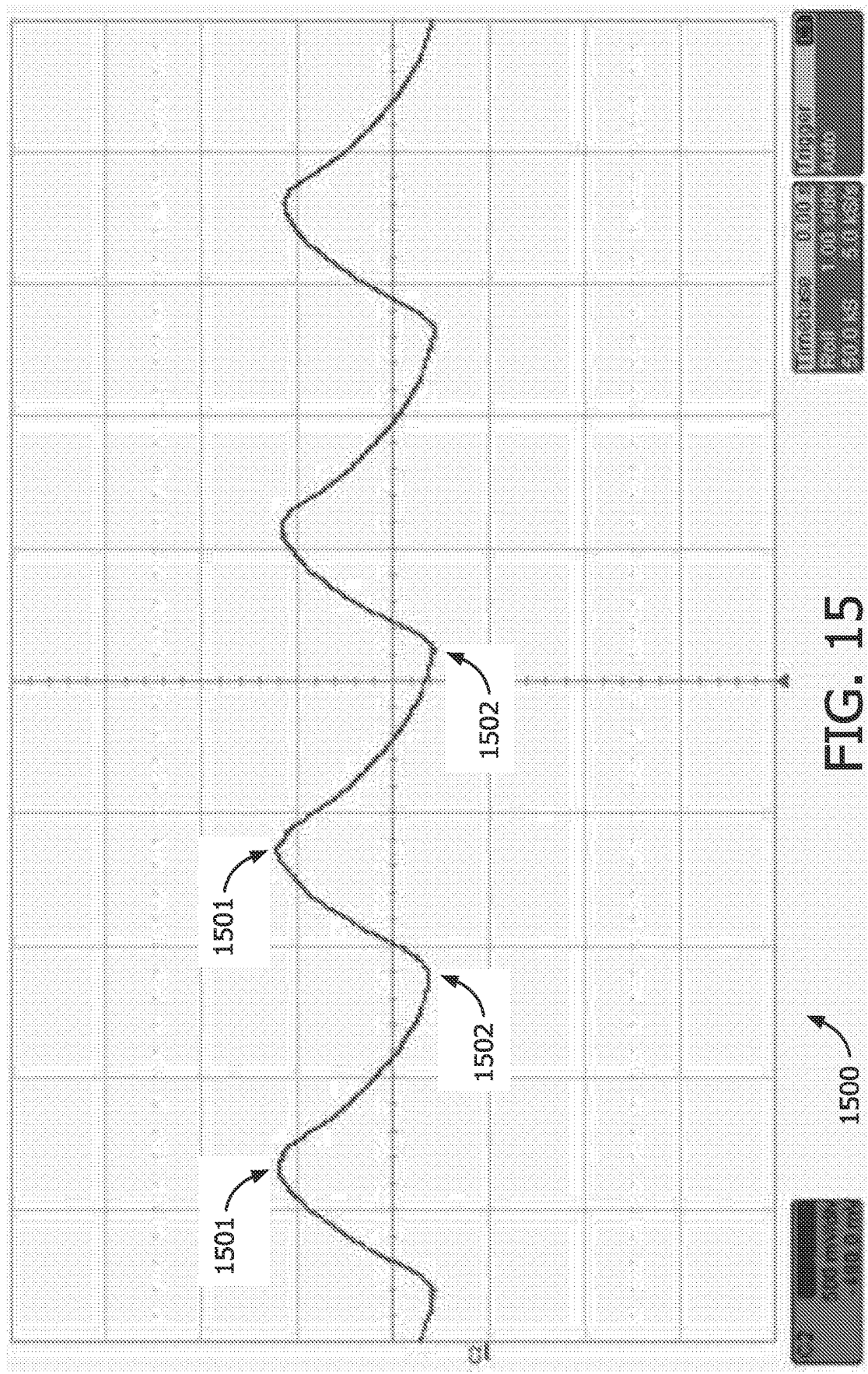
Figure 16:
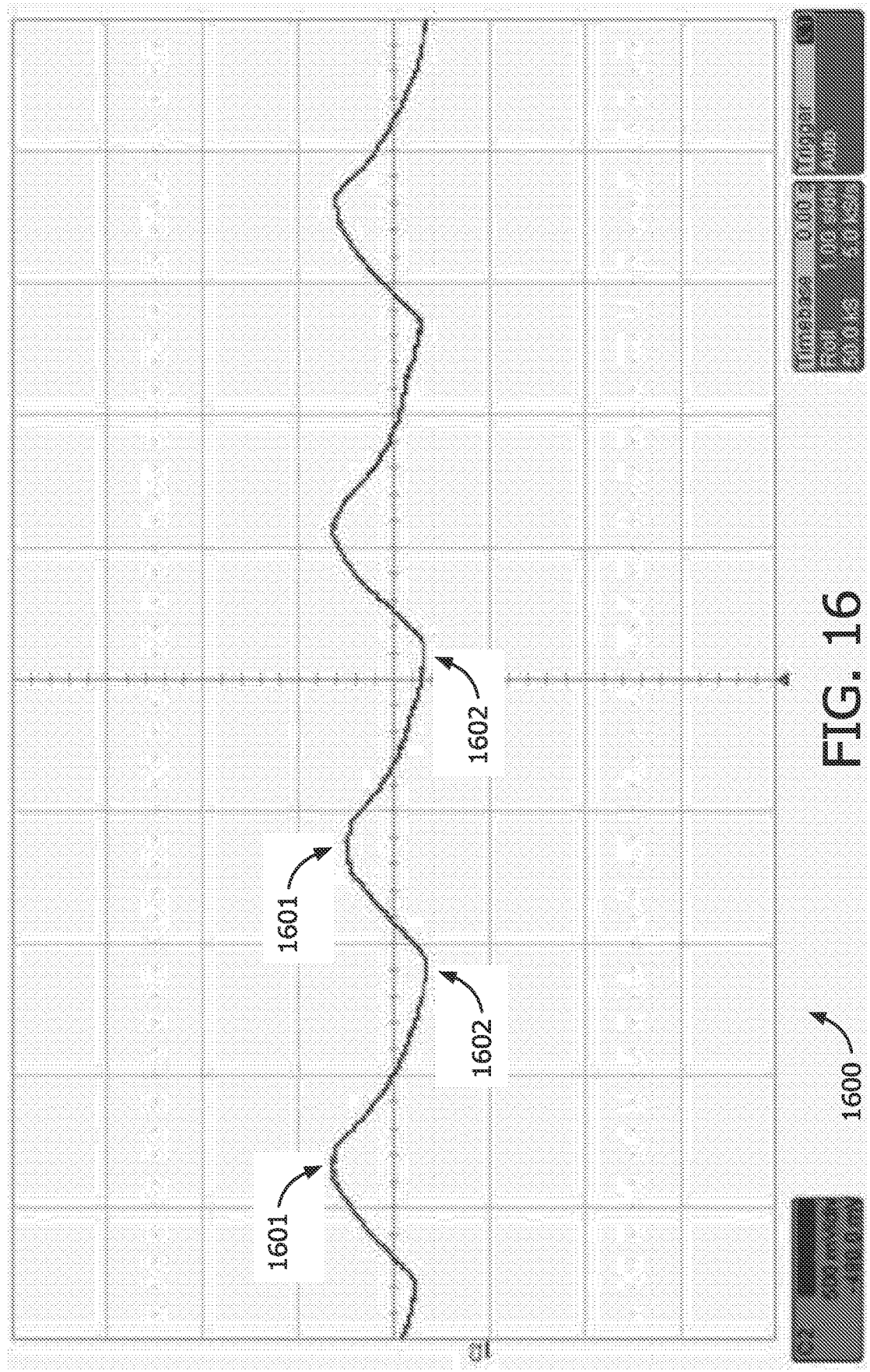

By way of illustration, FIG. 15 illustrates a voltage signal 1500 as may be produced by a subsystem the same as or similar to subsystem 1000 and 1000a (as described elsewhere herein in relation to FIGS. 10 and 11), through frequency-to-voltage circuit 1001 (FIG. 10), by using respiration as a source of ultrasonic energy. Voltage signal 1500 illustrates peaks 1501 and valleys 1502 corresponding to inhalations and exhalations, respectively. FIG. 15 depicts measurements taken using a sensor 142 (i.e. MEMS microphone) as a distance of about 1 foot from the subject. By way of further illustration, FIG. 16 illustrates a voltage signal 1600 as may be produced by a subsystem the same as or similar to subsystem 1000 and 1000a (as described elsewhere herein in relation to FIGS. 10 and 11), through frequency-to-voltage circuit 1001 (FIG. 10), by using respiration as a source of ultrasonic energy. Voltage signal 1600 illustrates peaks 1601 and valleys 1602 corresponding to inhalations and exhalations, respectively. FIG. 16 depicts measurements taken using a sensor 142 (i.e. MEMS microphone) as a distance of about 10 feet from the subject. Note that the value of the coupling capacitor (as described in relation to FIG. 11) may be adjusted based on the expected typical distance between sensor 142 and, in this case, subject 106.

In some implementations, sensor 142 may be configured to generate output signals conveying measurements related to gas parameters of respiratory airflow, parameters related to airway mechanics, and/or other parameters. Gas parameters may include flow, (airway) pressure, humidity, velocity, acceleration, and/or other gas parameters. Output signals may convey measurements related to respiratory parameters, including but not limited to respiratory timing and respiratory rate. Respiratory timing may include one or more of onset of inhalation, duration of inhalation, onset of respiratory pause between inhalation and exhalation, duration of respiratory pause, onset of exhalation, duration of exhalation, respiratory rate, and/or other timing characteristics related to respiration. Sensor 142 may be in fluid communication with conduit 180 and/or mouthpiece or mask 184. Sensor 142 may generate output signals related to physiological parameters pertaining to subject 106. Parameters may be associated with the state and/or condition of an airway of subject 106, the breathing of subject 106, the gas breathed by subject 106, the composition of the gas breathed by subject 106, the delivery of the gas to the airway of subject 106, and/or a respiratory effort by the subject.

Figure 10:
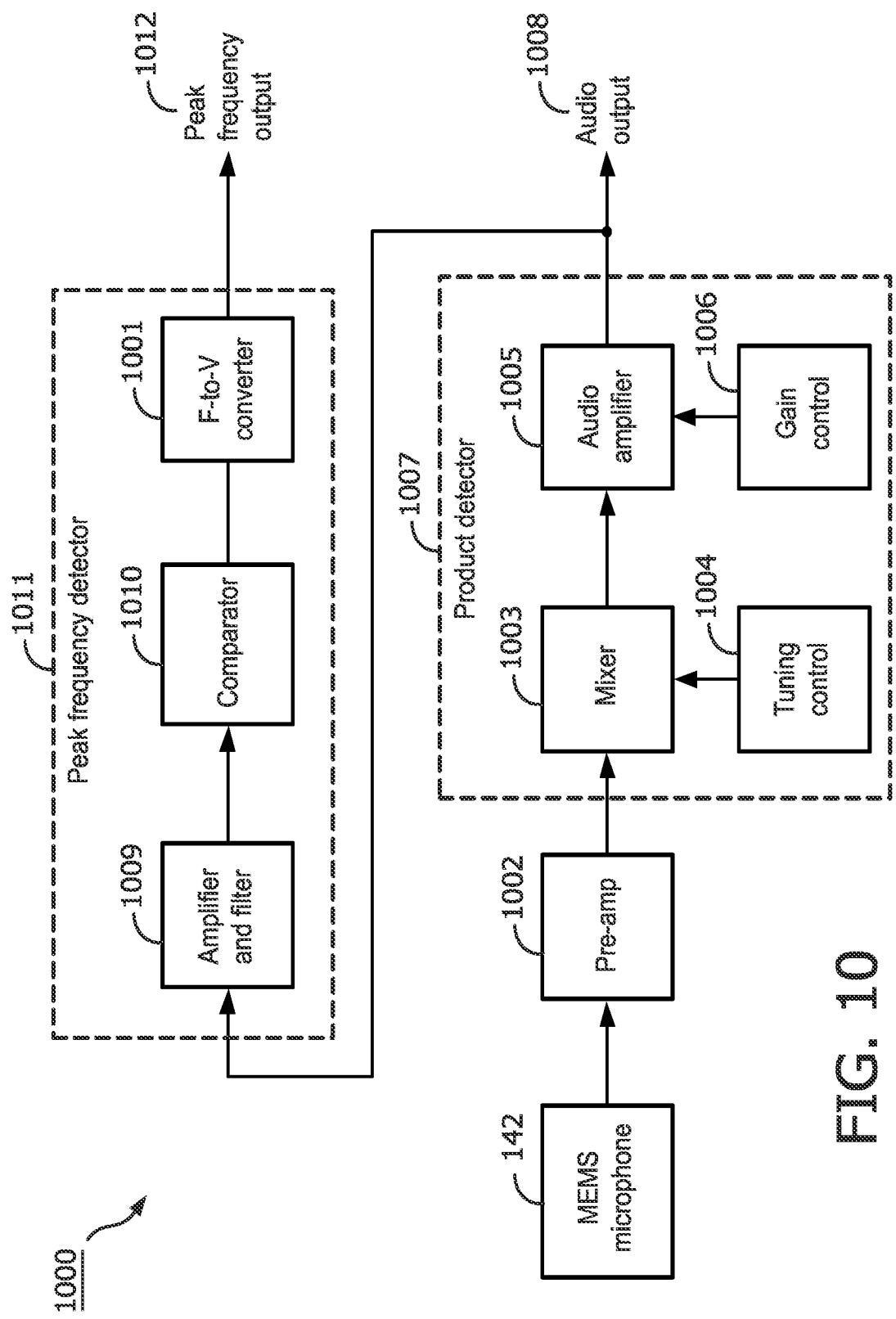
FIG. 10-11 illustrate subsystems for processing signals representing received ultrasonic energy as may be used in a system configured to deliver medicament to a subject.
Figure 11:
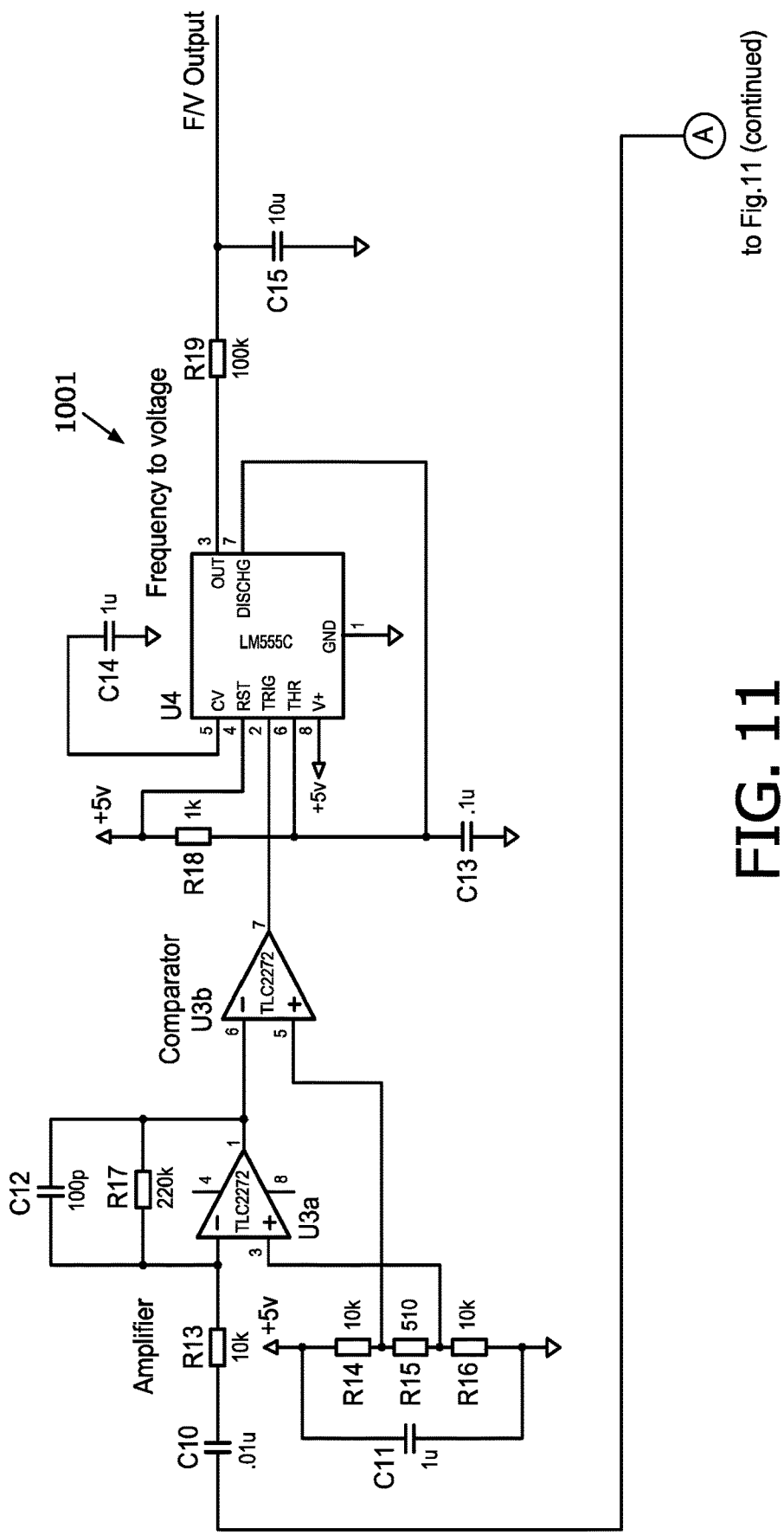
Figure 11:
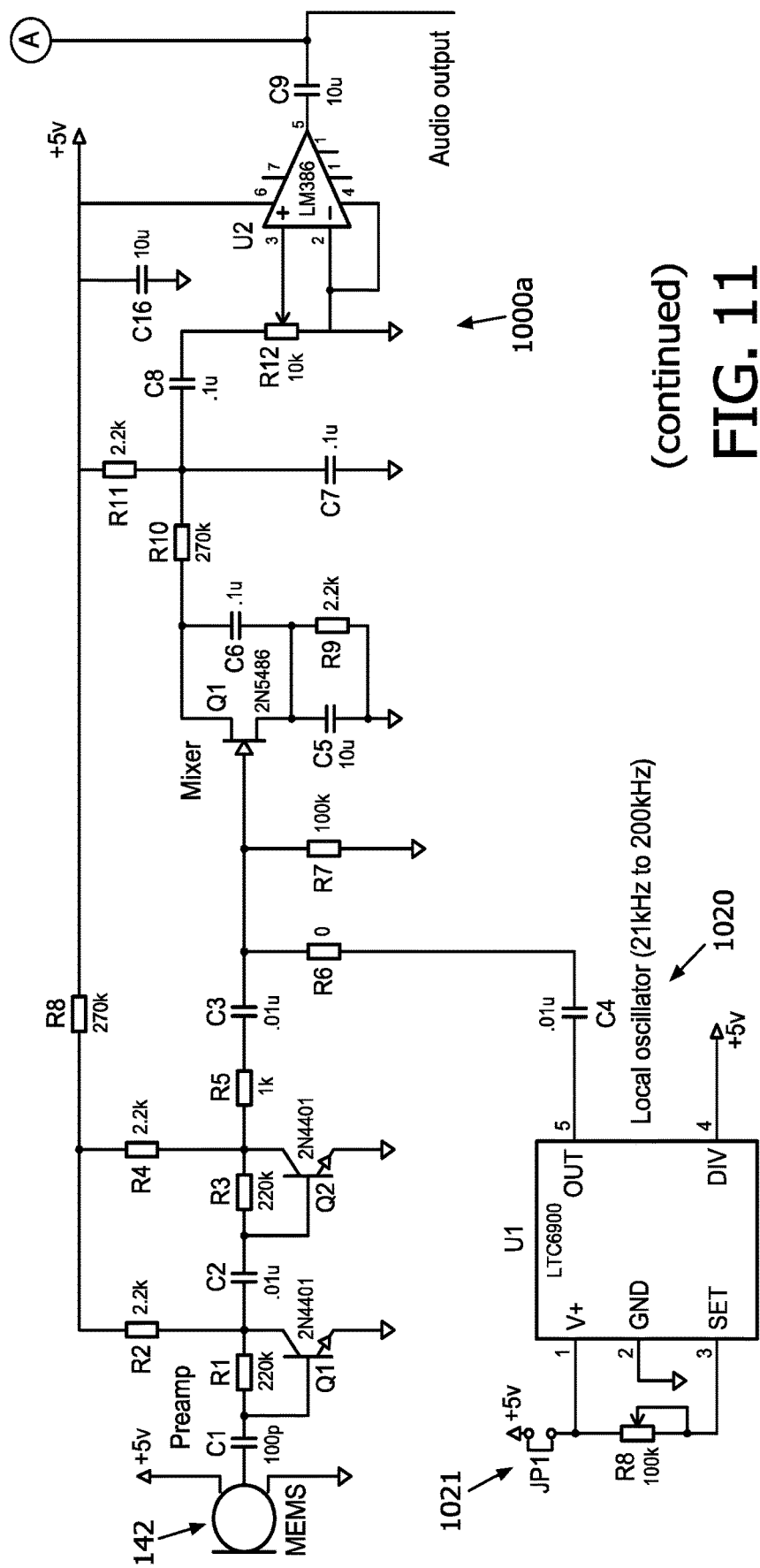

By way of illustration, FIGS. 10 and 11 schematically illustrate various components forming subsystems 1000 and 1000*a*, respectively. Subsystems 1000 and 1000*a* may include a frequency-to-voltage circuit 1001. Subsystems 1000 and 1000*a* may represent similar features and functionality. Subsystem 1000, subsystem 1000*a*, and/or components thereof may be included and/or used in embodiments of system 10 (FIG. 1). Acoustic and/or ultrasonic energy (including energy emitted by one or both of a respiratory device and/or subject 106) may be received and/or measured by microphone 142. A pre-amplifier 1002 may be configured to include a high pass filter and/or a coupling capacitor. Depending on the application, the coupling capacitor may range from about 100 pf (for short range measurements within about a 1 foot distance) to about 5600 pf (for longer range measurements between about 1 foot and about 10 feet distance). Pre-amplifier 1002 may be used before the incoming signal is amplified, for example as depicted in FIG. 11 by using two transistors. A product detector 1007 may be configured to detect the type of respiratory medicament delivery device is in operation, based on the measured ultrasonic energy. Product detector 1007 may include mixer 1003, tuning control 1004, audio amplifier 1005, gain control 1006, and/or other components. Mixer 1003 may include a transistor driven by both pre-amplifier 1002 and (as depicted in FIG. 11) a local oscillator 1020. Mixer 1003 may be configured to multiply its two inputs with the resulting output, thus producing sum and difference frequencies. Audio amplifier 1005 may be configured to amplify the signal created by mixer 1003 and/or to provide a comfortable listening level for a user listening to audio output 1008. Gain control may be configured to control gain for audio amplifier 1005. Output from audio amplifier 1005 may be transmitted to peak frequency detector 1011. Peak frequency detector 1011 may include an amp-and-filter 1009, a comparator 1010, a frequency-to-voltage circuit 1001, and/or other components. Peak frequency detector 1011 may be configured to generate a (direct current) output voltage that is proportional to the (dominant) frequency as received through microphone 142. Amp-and-filter 1009 may provide additional amplification and filtering of the signal prior to comparator 1010 digitizing it. The resulting pulse train may be used to trigger a pulse entering a capacitor, thus adding charge to the capacitor. The charge on the capacitor may represent the (dominant) frequency as received through microphone 142. Alternatively, and/or simultaneously, such a pulse train may be used to increment a timer and/or counter, to provide similar utility as the capacitor.

In some implementations, subsystems the same as or similar to subsystems 1000 and 1000*a* may be used as narrow-band special-purpose microphones. For example, the emitted ultrasonic energy for mesh nebulizers and dry-powder inhalers may be a narrow-band signal for which subsystems 1000 and 1000*a* as depicted may be suitable.

Figure 6:
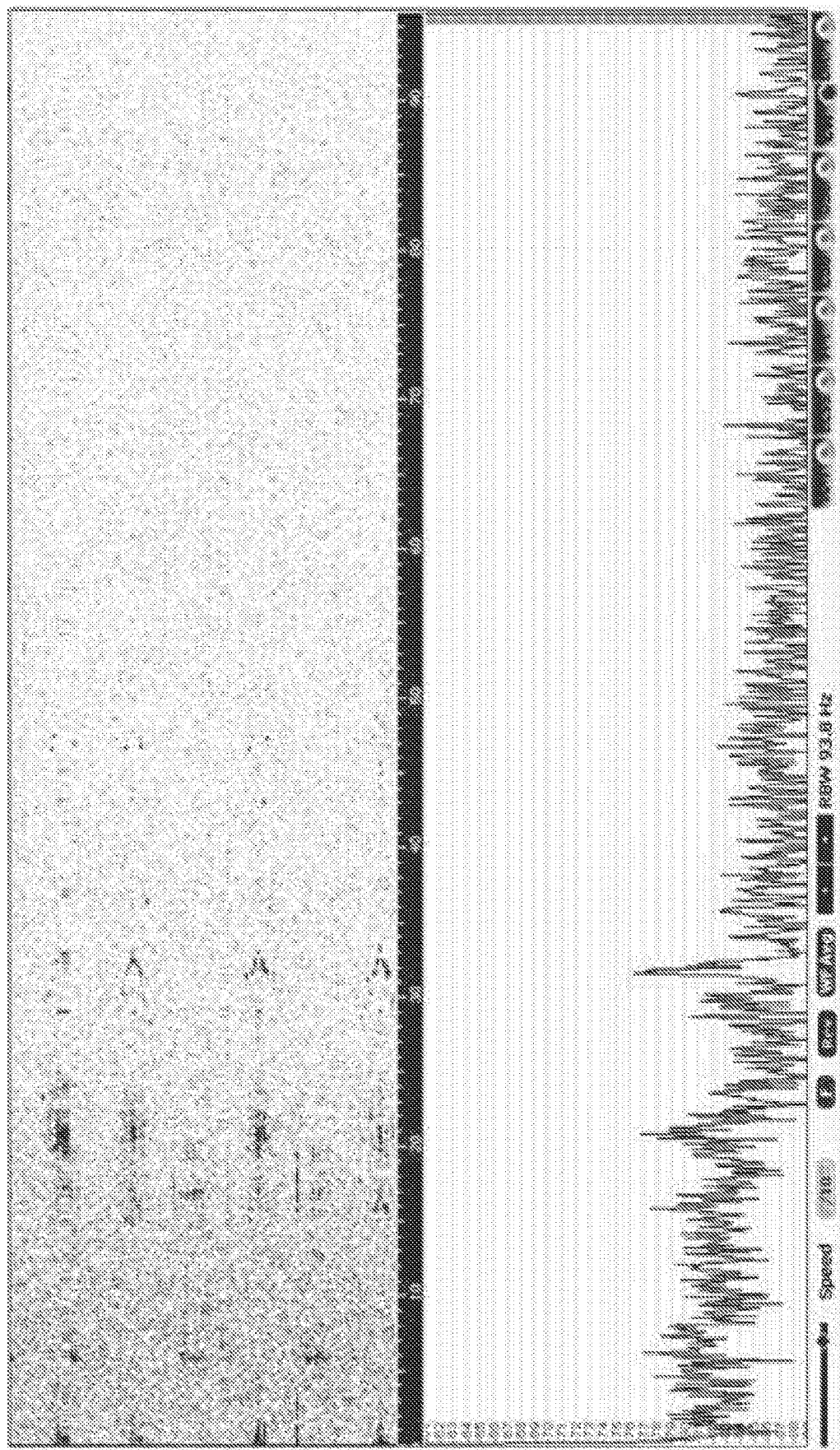
Figure 7:
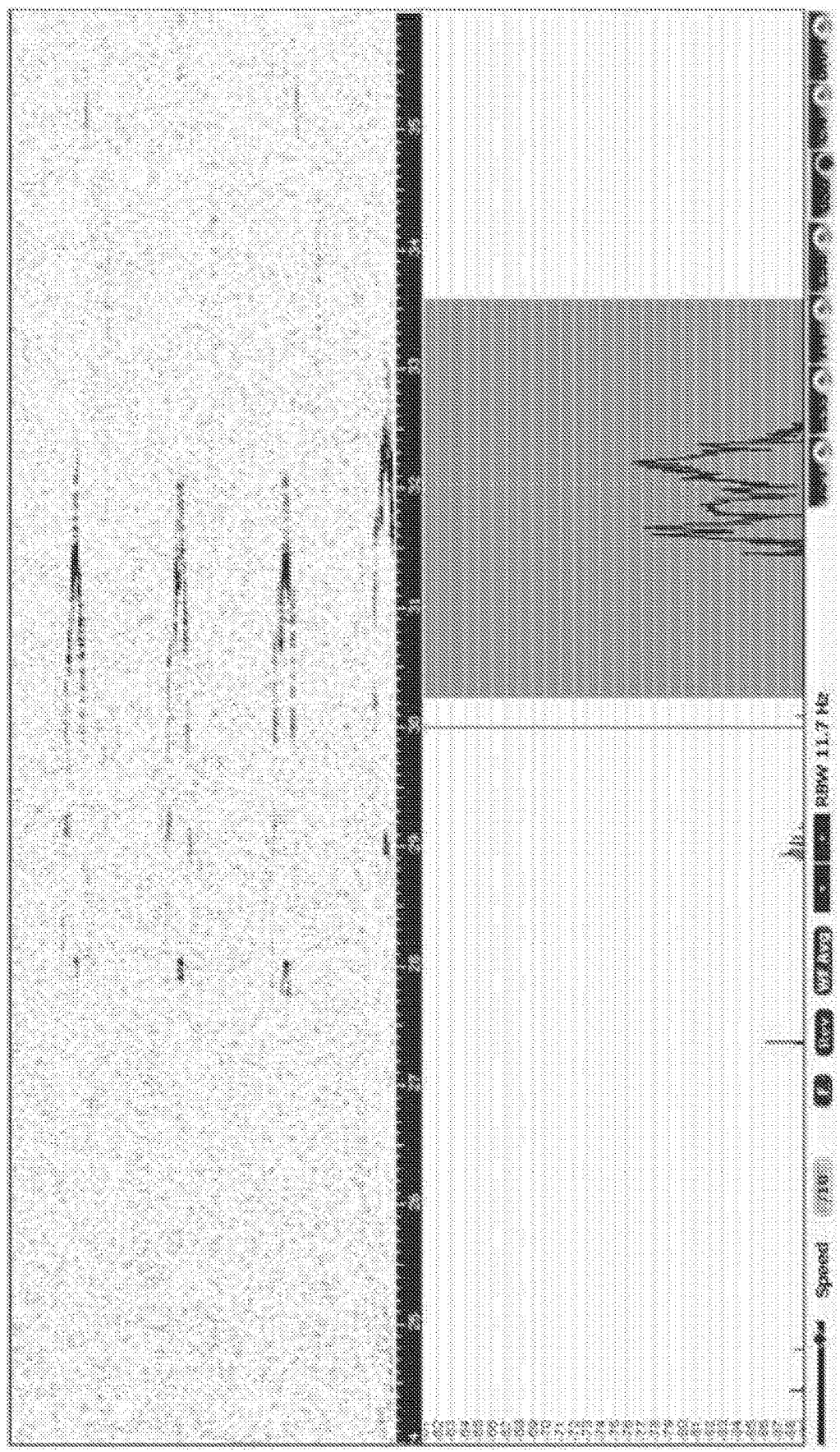
Figure 8:
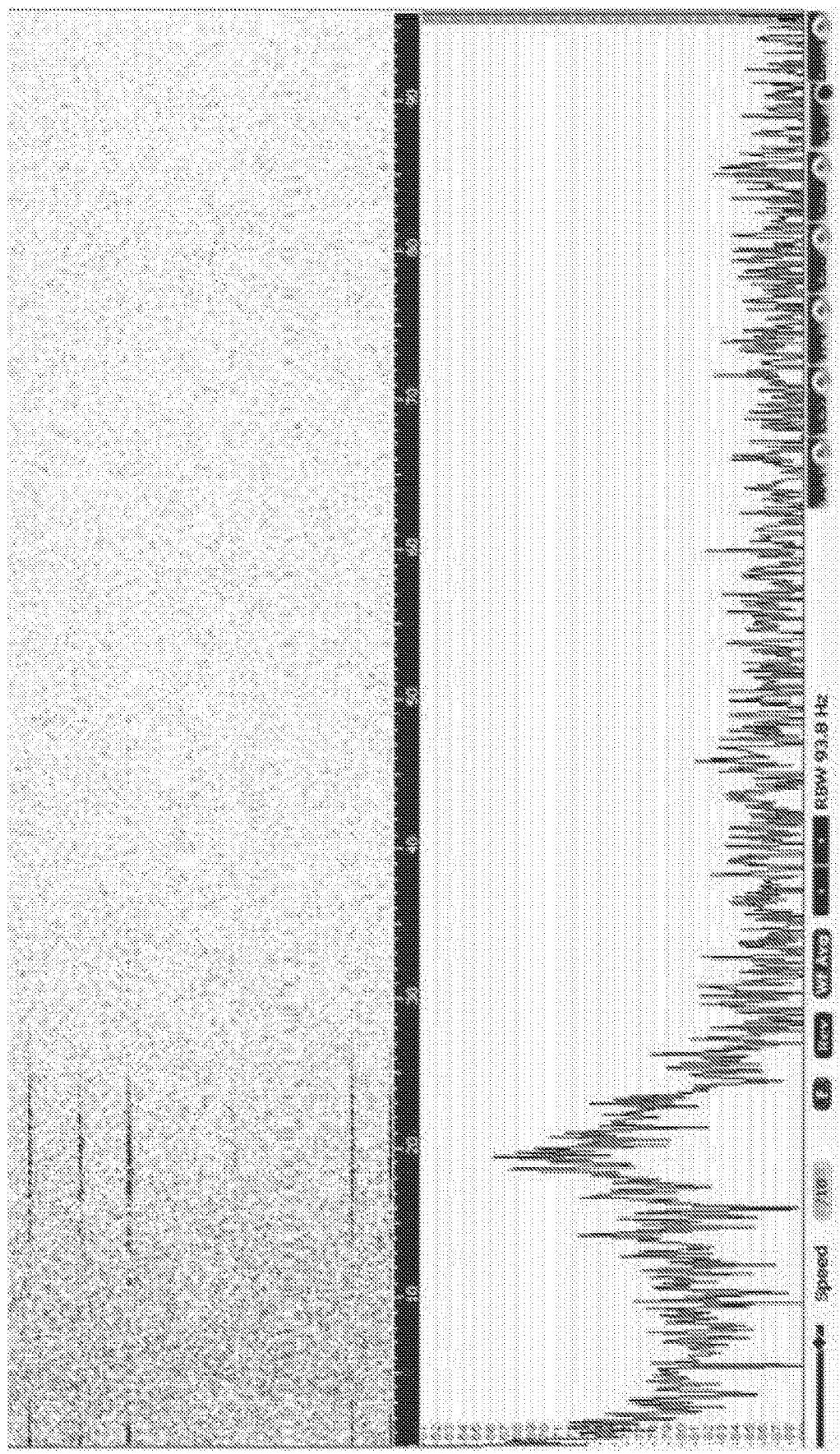
Figure 17:
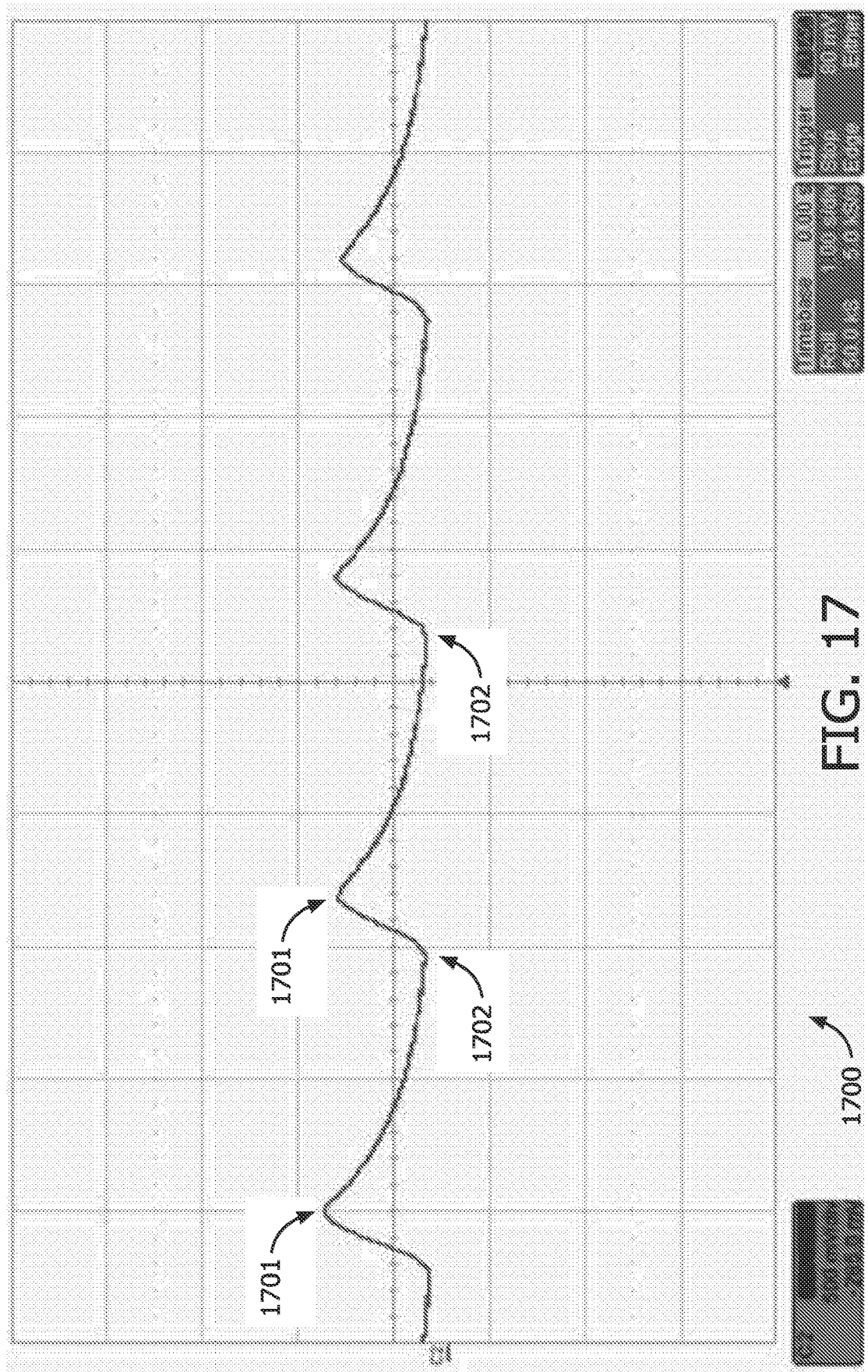

By way of illustration, FIGS. 6 and 7 illustrate graphs 600 and 600*a* for energy emitted during the operation of a dry-powder inhaler. Graphs 600 and 600*a* include a waterfall display in the top half, and a magnitude (of energy amplitude) in the bottom half. The waterfall display shows time on the vertical axis and measured frequency (in kHz) on the horizontal axis. As depicted in FIG. 6, graph 600 includes a narrow peak magnitude 601 near a frequency of 31 kHz, which may be an ultrasonic energy signature for the delivery of medicament through the dry-powder inhaler. This energy may be emitted as air rushes past a drug capsule and/or by resonance within a respiratory device during operation. The top half of graph 600 depicts three distinct ultrasonic whistles, each associated with a single inhalation event, that each begin at about 31 kHz, increase smoothly to about 33 kHz, and then return smoothly to about 31 kHz. FIG. 7 illustrates a magnified view of a section depicted in FIG. 6. By way of further illustration, FIG. 17 illustrates a voltage signal 1700 as may be produced by a subsystem the same as or similar to subsystem 1000 and 1000*a* (as described elsewhere herein in relation to FIGS. 10 and 11), through frequency-to-voltage circuit 1001 (FIG. 10). Voltage signal 1700 may be produced by measuring ultrasonic energy emitted by a subject using a dry-powder inhaler. Voltage signal 1700 illustrates peaks 1701 and valleys 1702 corresponding to inhalations and exhalations, respectively. In this example, the peak emissions near a frequency of 31 kHz (from the dry-powder inhaler) are shifted down by a subsystem the same as or similar to subsystem 1000 and 1000*a* (as described elsewhere herein in relation to FIGS. 10 and 11) to about 20 kHz, and supplied to frequency-to-voltage circuit 1001 (FIG. 10). The resulting sum and difference frequencies would then be a high of 51 kHz+31 kHz=82 kHz and a low of 51 kHz−31 kHz=20 kHz. Peaks 1701 and valleys 1702 are relative to this low signal of about 20 kHz. FIG. 17 illustrates detection of inhalation and exhalation for a subject using a dry-powder inhaler.

Figure 12:
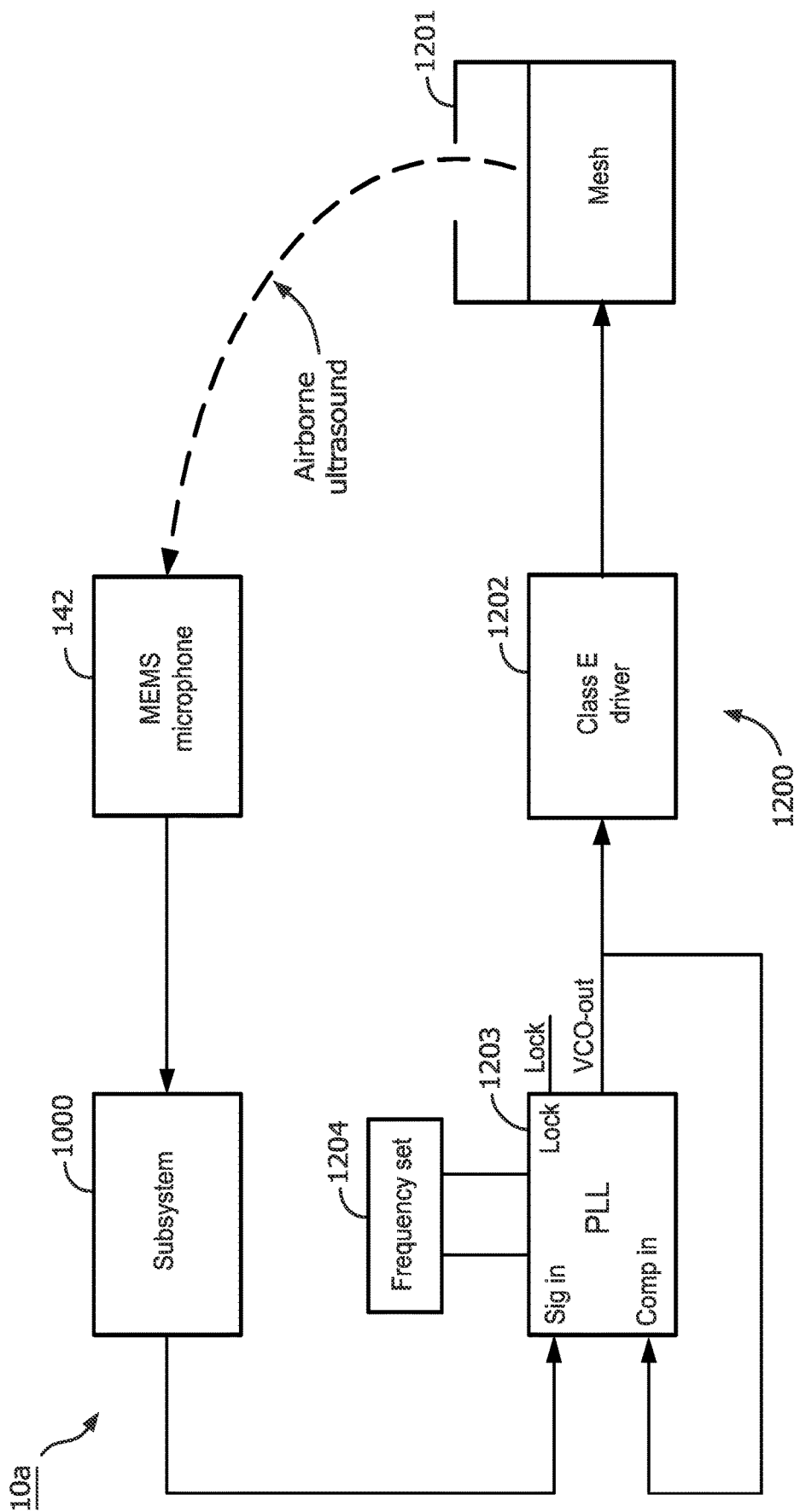

Referring to FIGS. 10 and 11, subsystems the same as or similar to subsystems 1000 and 1000*a* may be used in a larger system configured to deliver respiratory therapy to a subject, such as system 10 (FIG. 1) and/or systems similar to system 10. By way of illustration, FIG. 12 schematically illustrates a system 10*a* that includes a mesh nebulizer 1200, microphone 142, subsystem 1000, and/or other components. Mesh nebulizer 1200 may include a mesh 1201, a class E driver 1202, a phase-locked loop circuit (PLL) 1203, and/or other components. PLL 1203 may include inputs "signal in" and "comparator in," and outputs "VCO-out" and "lock," all of which are standard for PLLs. Note that output VCO-out may loop back to input "comparator in." PLL 1203 may be configured to provide a driving frequency for mesh 1201 (through a suitable driver such as Class E driver 1202) and/or a piezoelectric element connected to mesh 1201. In some implementations, PLL 1203 may be configured to adjust the driving frequency based on a phase difference between the ultrasonic energy measured through microphone 142 and the signal/frequency used to drive mesh 1201 (e.g. from output VCO-out). Note that microphone 142 may need to be positioned such that contact with aerosol is avoided or minimized, e.g. by placing microphone 142 at a suitable harmonic distance (i.e. one or more cycles) from mesh 1201. Note that the signal from output VCO-out may be a square wave (or similar to a square wave), whereas the signal from mesh 1201 may be a sinusoid, although their frequencies are necessarily the same.

In some implementations, a phase difference between the ultrasonic energy measured through microphone 142 and the signal/frequency used to drive mesh 1201 (e.g. from output VCO-out) may be caused by one or more changes in environmental and/or ambient conditions, including but not limited to temperature, humidity, and/or chemical composition of a gas (including but not limited to the percentage of $CO_2$ in a particular volume of gas).

Figure 18:
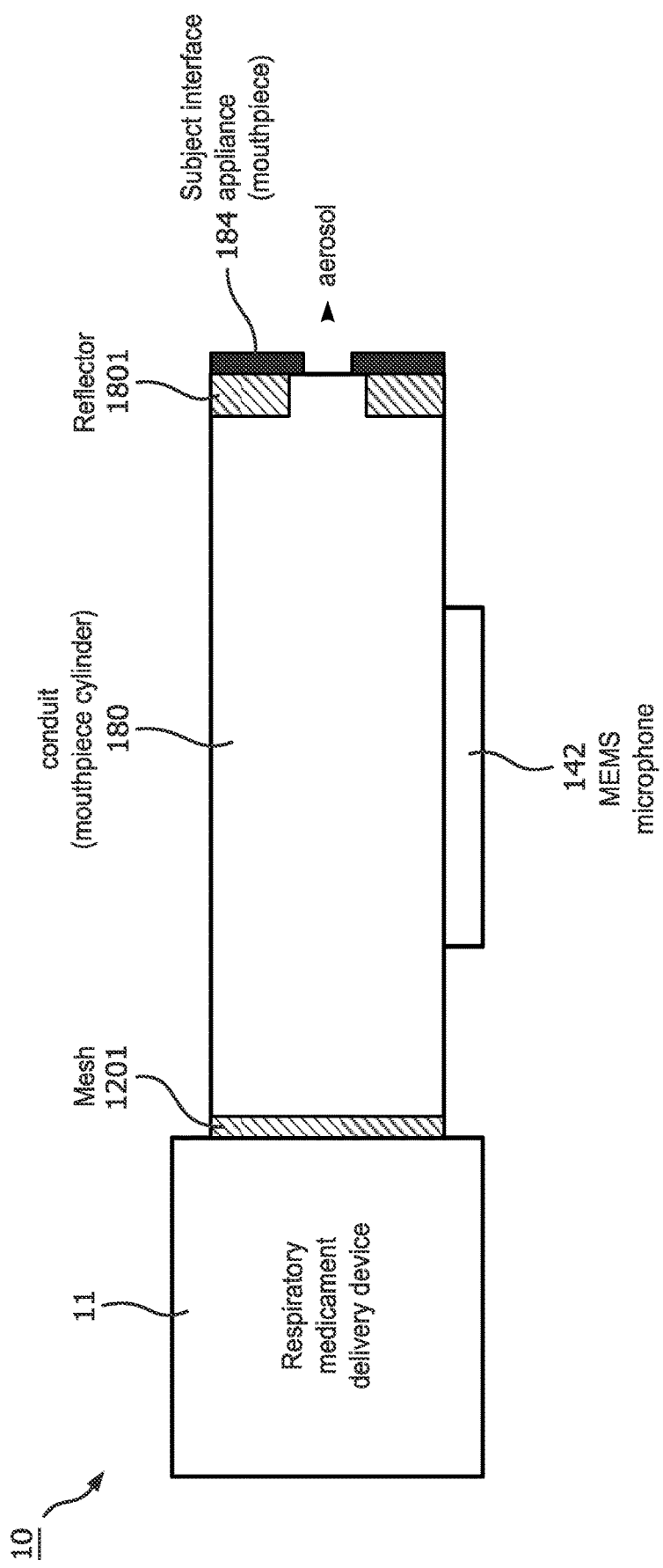

By way of illustration, FIG. 18 illustrates a system 10 comprising a respiratory medicament delivery device 11 that includes a mesh 1201, and which includes a conduit 180

(also referred to a mouthpiece cylinder 180) configured to fluidly couple mesh 1201 to a subject interface appliance 184 (also referred to as mouthpiece or mask 184) for aerosol delivery (indicated by the dotted arrow in FIG. 18). As a subject exhales into conduit 180, one or more environmental and/or ambient conditions may change. For example, the temperature within conduit 180 may increase, which may change the speed of ultrasonic energy propagation within conduit 180 and/or otherwise change the acoustic impedance within conduit 180. Responsive to such respiratory actuation a phase difference between the ultrasonic energy measured through microphone 142 and the signal/frequency used to drive mesh 1201 (e.g. from output VCO-out) may change. Alternatively, and/or simultaneously, as a subject inhales ambient air (and aerosol) into conduit 180, one or more environmental and/or ambient conditions may change. For example, the temperature within conduit 180 may decrease. Responsive to such respiratory actuation the phase difference between the ultrasonic energy measured through microphone 142 and the signal/frequency used to drive mesh 1201 (e.g. from output VCO-out) may change. Note that microphone 142 need not be placed in close proximity to mesh 1201 or subject interface appliance 184, but may be positioned in various locations along conduit 180.

In some implementations, system 10 as depicted in FIG. 18 may include one or more reflectors 1801 and/or reflective surfaces within conduit 180. For example, a hard surface such as copper of glass may be suitable to reflect ultrasonic energy. With proper arrangement of mesh 1201 to reflector 1801, standing waves may be established within conduit 180 during operation of system 10. Microphone 142 may be placed at or near a point within conduit 180 where the signal strength is increased by virtue of the reflected ultrasonic energy.

In some implementations, PLL 1203 may be configured to provide an initial driving frequency for mesh 1201. For example, the initial driving frequency may be above the resonant frequency of mesh 1201 such that aerosol production by system 10a is reduced in order to reduce waste of medicament during a period of non-inhalation by subject 106. For example, the initial driving frequency may be 105%, 110%, and/or another suitable percentage of the resonant frequency of mesh 1201 that is sought to be used for aerosol production. The reduction in aerosol production may be any percentage between 100% and 0% of the maximum aerosol production level. During inhalation of subject 106, sensor 142 will receive and/or pick up ultrasonic energy emitted by the airway of subject 106, as described elsewhere herein. System 10a may be configured such that generated output signals conveying information related to ultrasonic energy emitted by both a respiratory device and subject 106 cause PLL 1203 to change its driving frequency. In particular, this changed driving frequency may be the resonant frequency of mesh 1201 such that aerosol is produced by system 10a. Subsequently, responsive to the end of a particular inhalation, system 10a may return to operating conditions such that aerosol production is reduced. By way of non-limiting example, PLL 1203 may be configured to lock when ultrasonic energy that is indicative of an inhalation by subject 106 is (detected to be) present. Under these conditions aerosol may be generated and delivered. PLL 1203 may be configured to go out of lock when ultrasonic energy that is indicative of an inhalation by subject 106 is (detected to be) absent. Under these conditions, aerosol production may be reduced and/or suppressed, thus effectuating a breath-activated mode of operation.

PLL 1203 may be configured, once it is locked, to adjust operating conditions such that the phase difference is minimized, and the energy amplitude (at least locally) maximized. The features described in this disclosure may be used to detect conditions including sputter, end of treatment, and/or other conditions.

Figure 13:
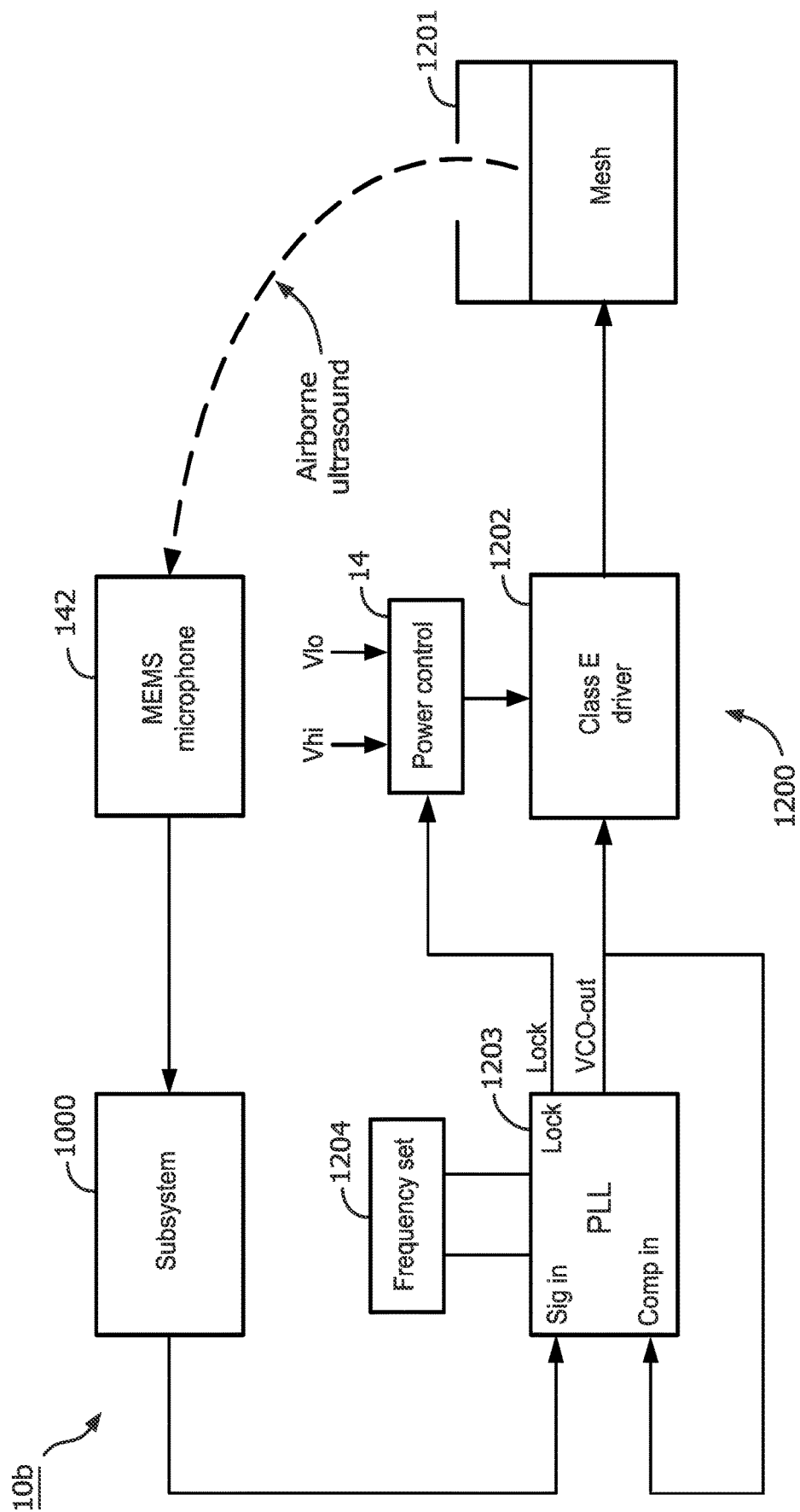
Figure 14:
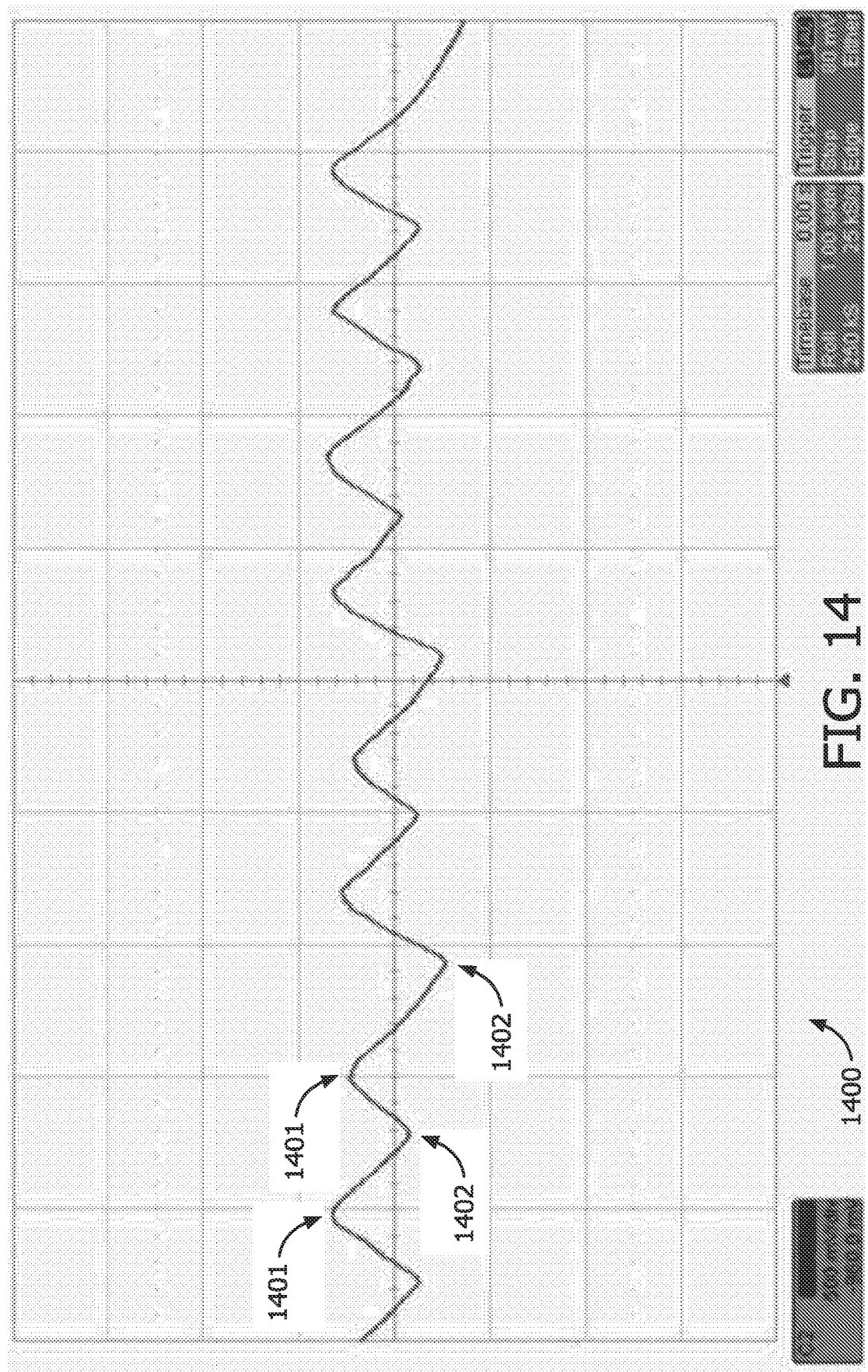
FIGS. 14-17 illustrate a voltage signal as may be produced by a system configured to deliver respiratory therapy, the voltage signal corresponding to measured ultrasonic energy.

In some implementations, PLL 1203 may be configured to provide a driving frequency that matches and/or tracks the resonant frequency of mesh 1201 regardless of the absence or presence of ultrasonic energy that is indicative of an inhalation by subject 106. In such a case, PLL 1203 may lock when ultrasonic energy that is indicative of an inhalation is present, and PLL 1203 may go out of lock when ultrasonic energy that is indicative of an inhalation is not present. The lock signal of PLL 1203 may be used to reduce aerosol production by the system. By way of illustration, such a system is depicted in FIG. 13. The lock signal may be used to control when to reduce and/or suppress aerosol production, thus effectuating a breath-activated mode of operation.

Referring to FIG. 13, in some implementations, system 10b may include power control 14. Power control 14 may be controlled based on, at least in part, an output from PLL 1203, such as, e.g., the lock output. When PLL 1203 is locked, e.g. during inhalation, power control 14 may be configured to control Class E driver 1202 to use a high power setting (interchangeably referred to as "high power level" or "high operational power level") that is sufficient for system 10b to produce aerosol. When PLL 1203 is not locked, a low power setting (interchangeably referred to as "low power level" or "low operational power level") may be used. For example, when PLL 1203 is not locked, it may output the same (or similar) frequency but at such low power that little or no aerosol is produced. Power control 14 may be configured to provide gain control for Class E Driver 1202, and thus for mesh 1201. Implementations that combine features from, e.g., the systems depicted in FIG. 12 and FIG. 13 may be contemplated within the scope of this disclosure. As used herein, the phrase "operational power level" may refer to the level of power used during operation of a system (e.g. system 10, system 10a, system 10b, etc.), including but not limited to the level of power used to drive piezoelectric element 102, mesh 1201, and/or other means that provide mechanical vibration or displacement of a medium.

If and/or when the operating frequency of mesh 1201 changes away from resonance, the energy emitted by mesh 1201 will decrease in amplitude (due to the impedance curve of the element used to drive mesh 1201), effectively increasing the phase difference. In response, PLL 1203 may adjust its output frequency to counteract this condition. Contrary to respiratory devices that are intentionally driven at a frequency other than their resonance frequency (e.g. to avoid frequency adjustments on the opposite side of the impedance curve), the systems disclosed herein may operate much closer to the resonance frequency, e.g. letting PLL 1203 track changes in operation based on the signals generated by microphone 142. In some implementations, mesh nebulizer 1200 may include a frequency set 1204 configured to manually and/or programmably control PLL 1203.

Figure 3:
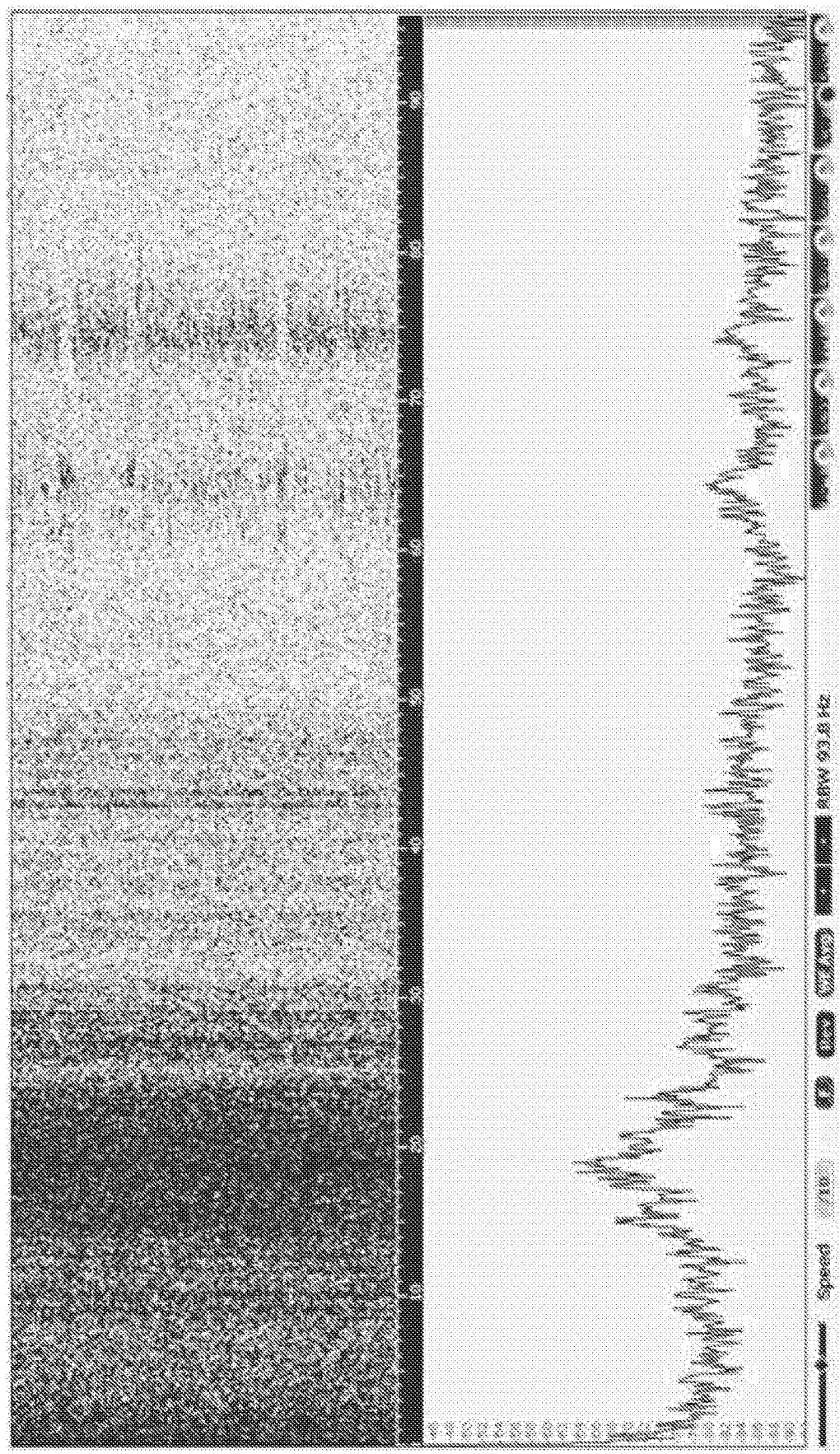
FIGS. 3-9 illustrate graphs for energy emitted during the operation of various respiratory medicament delivery devices as may be used in a system configured to deliver respiratory therapy to a subject.
Figure 4:
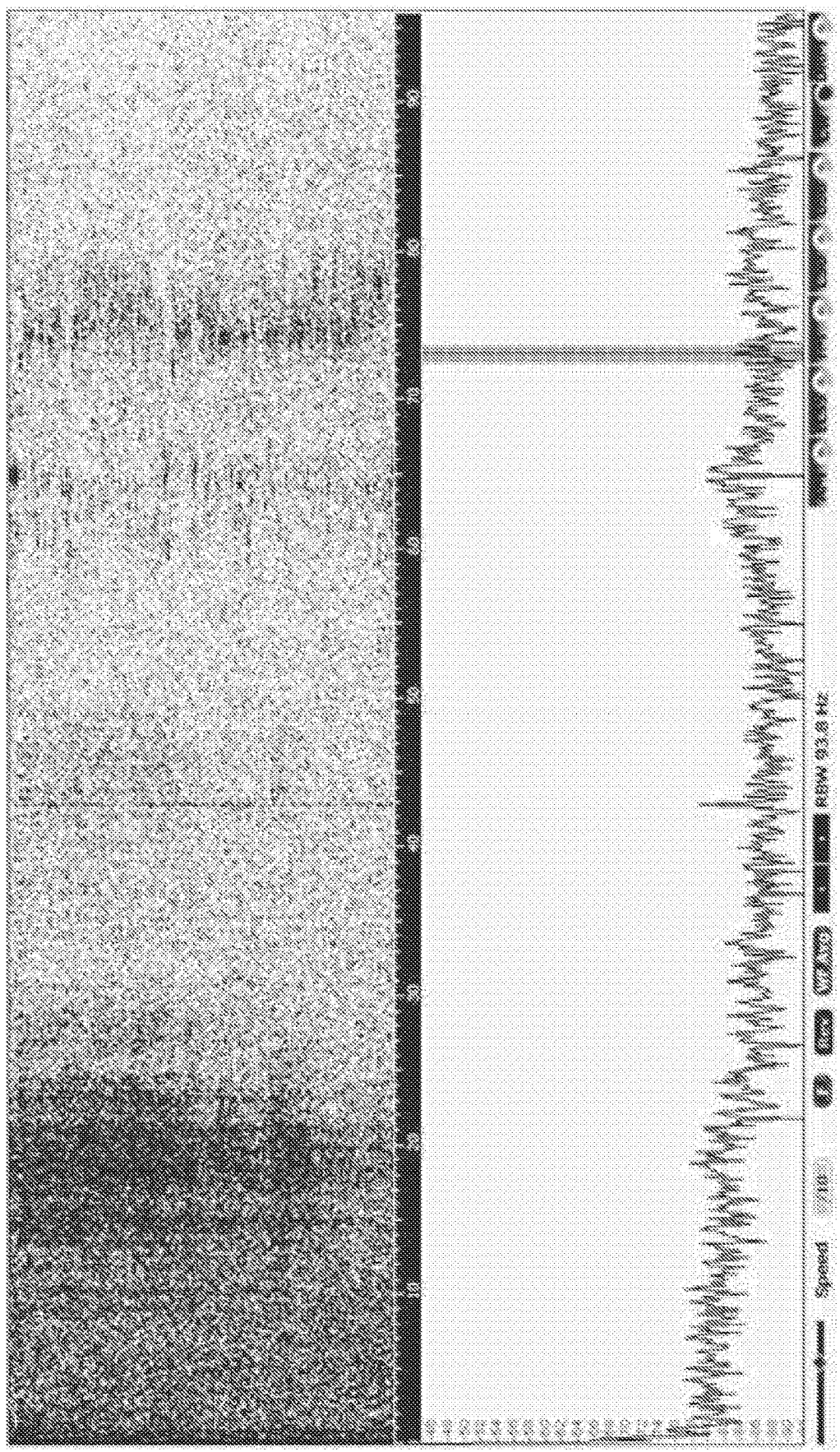
Figure 5:
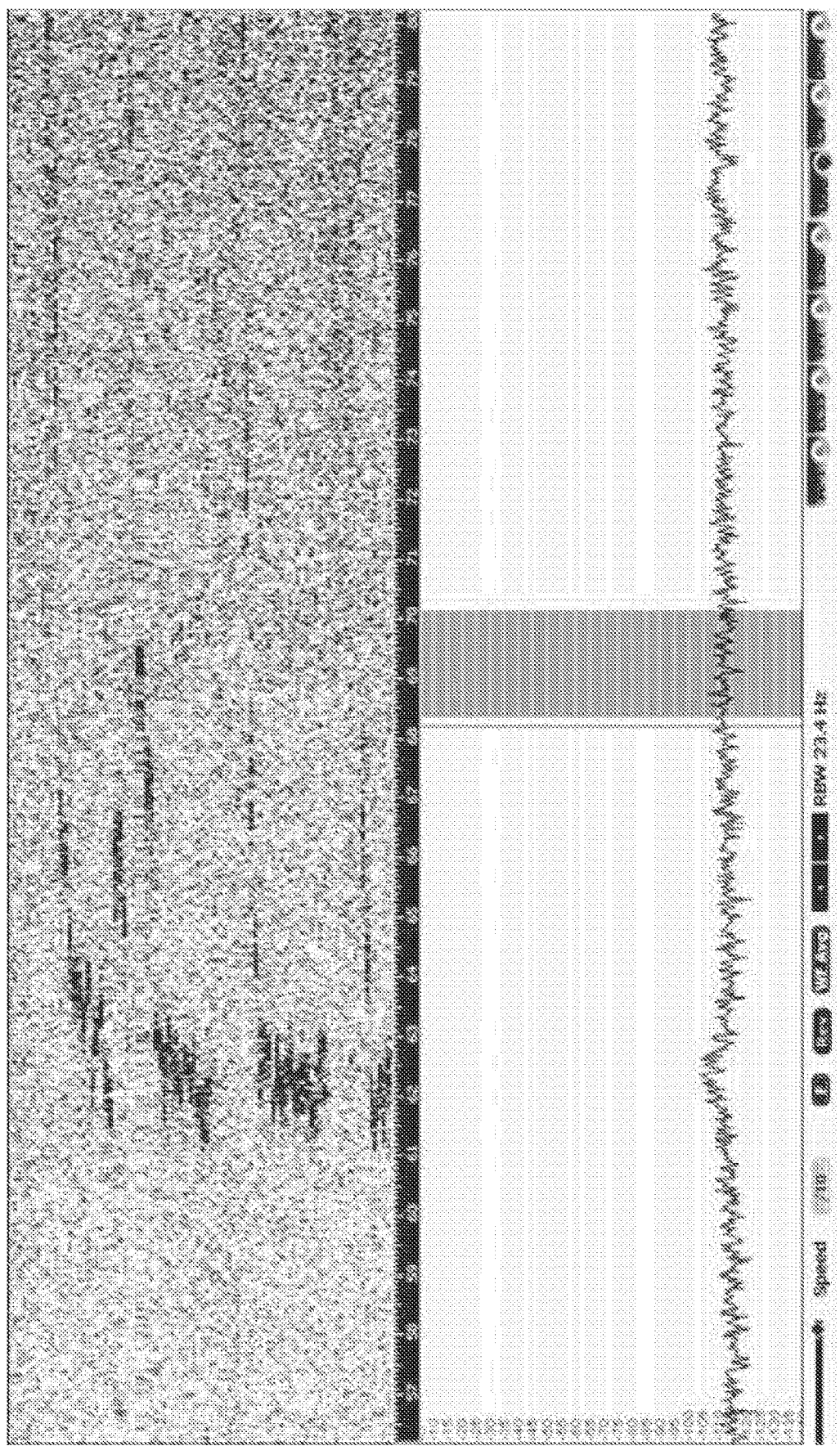

Referring to FIG. 1, in some implementations, respiratory medicament delivery device 11 may include a jet nebulizer and/or components/features thereof. Jet nebulizers may include compressed air. The emitted ultrasonic energy for some types of respiratory medicament delivery devices, including but not limited to jet nebulizers, may be a wideband signal. Such a signal may be measured using a subsystem such as subsystem 1000a in FIG. 11, but with jumper 1021 removed (and resistor R9 changed from 10 kOhm to 2 kOhm), and thereby not using product detector 1007 (as depicted in FIG. 10) or local oscillator 1020 (as depicted in FIG. 11). In this mode of operation, the subsystem may be suitable for wide-band signals between about 15 kHz and about 65 kHz. By way of illustration, FIGS. 3 and 4 illustrate graphs 300 and 300a for energy emitted during the operation of a jet nebulizer. Graphs 300 and 300a include a waterfall display in the top half, and a magnitude (of energy amplitude) in the bottom half. The waterfall display shows time on the vertical axis and measured frequency (in kHz) on the horizontal axis. As depicted in FIG. 3, graph 300 includes a wide band signal 303 between about 15 kHz and about 21 kHz, which appeared after liquid medicament was added to the jet nebulizer. Note that distinct peaks 301 and 302 in energy magnitude appear at about 64 kHz and 74 kHz, respectively. FIG. 4 illustrates operation of a jet nebulizer at the commencement of sputter. Information derived from graphs such as graphs 300 and 300*a* may be used to control operation of a respiratory medicament delivery device and/or monitor respiratory parameters (e.g. as indicative of patient adherence).

Referring to FIG. 1, in some implementations, the one or more sensors 142 may be configured to generate output signals conveying information related to one or more characteristics of ultrasonic energy emitted from the airway of subject 106, in particular during inhalation. Due to human physiology, the flow of air is different during inhalation and exhalation. As a result, (ultrasonic) energy emitted by a subject may be different between inhalation and exhalation. Inhalation through nasal pathways and/or (nasal) restrictions may cause ultrasonic energy to be emitted. For example, air flowing through nasal restrictions may produce ultrasonic whistles between about 60 kHz and about 75 kHz. By way of illustration, FIG. 5 illustrates a graph 500 depicting such ultrasonic whistles. Graph 500 includes a waterfall display in the top half, and a magnitude (of energy amplitude) in the bottom half. The waterfall display shows time on the vertical axis (in this case about 2 seconds) and measured frequency (in kHz) on the horizontal axis. As depicted, graph 500 includes a signal 501 between about 61 kHz and about 70 kHz. Information derived from graphs such as graph 500 may be used to control operation of a respiratory medicament delivery device and/or monitor respiratory parameters (e.g. as indicative of patient adherence). For example, such information may be used to control delivery of medicament to subject 106. This may avoid wasting medicament during exhalation. By way of further illustration, a subsystem the same as or similar to subsystem 1000 and 1000*a* (FIGS. 10 and 11) may, through frequency-to-voltage circuit 1001 (FIG. 10), produce a voltage signal such as voltage signal 1400 in FIG. 14, using the signal depicted in graph 500 of FIG. 5 as input. Voltage signal 1400 illustrates the same or similar ultrasonic whistles (having peaks 1401 and valleys 1402 corresponding to the range of frequencies of signal 501 depicted in FIG. 5) during an inhalation of a subject as depicted in graph 500 of FIG. 5.

Note that a breath-actuated mode of operation as described in relation to the systems depicted in FIGS. 12 and 13 may be used for different types of respiratory therapy delivery devices. In some implementations, a system similar to system 10*b* in FIG. 13 may not need a power control such as power control 14.

Information derived from a graph such as graph 500 (or any of the other examples described herein) may be used to determine device actuation, respiratory timing, inhalation period, exhalation period, flow rate, strength of inhalation by a patient, amount of drug delivered, number of drug delivery sessions in a day or week, etc. Based on a comparison of such measured information and the recommended treatment for a subject, a level of patient adherence may be determined. Combination of different types of derived information is contemplated within the scope of this disclosure. For example, device actuation information may be combined with patient-specific respiratory information to determine parameters and/or metrics related to patient adherence.

Referring to FIG. 1, in some implementations, respiratory medicament delivery device 11 may include a metered-dose inhaler and/or components/features thereof. The emitted ultrasonic energy for meter-dose inhalers may be a (brief) wide-band signal. Such a signal may be measured using a subsystem such as subsystem 1000*a* in FIG. 11, but with jumper 1021 removed (and resistor R9 changed from 10 kOhm to 2 kOhm), and thereby not using product detector 1007 (FIG. 10) or local oscillator 1020 (FIG. 11). In this mode of operation, the subsystem may be suitable for wide-band signals between about 15 kHz and about 65 kHz. By way of illustration, FIG. 8 illustrates a graph 800 for energy emitted during the operation of a metered-dose inhaler. Graph 800 includes a waterfall display in the top half, and a magnitude (of energy amplitude) in the bottom half. The waterfall display shows time on the vertical axis and measured frequency (in kHz) on the horizontal axis. As depicted in FIG. 8, graph 800 includes a brief wide band signal 801 between about 15 kHz and about 25 kHz. Information derived from graphs such as graph 800 may be used to control operation of a respiratory medicament delivery device and/or monitor respiratory parameters (e.g. as indicative of patient adherence).

Returning to FIG. 1, electronic storage 130 of system 10 comprises electronic storage media that electronically stores information. The electronic storage media of electronic storage 130 may include one or both of system storage that is provided integrally (i.e., substantially non-removable) with system 10 and/or removable storage that is removably connectable to system 10 via, for example, a port (e.g., a USB port, a FireWire port, etc.) or a drive (e.g., a disk drive, etc.). Electronic storage 130 may include one or more of optically readable storage media (e.g., optical disks, etc.), magnetically readable storage media (e.g., magnetic tape, magnetic hard drive, floppy drive, etc.), electrical charge-based storage media (e.g., EPROM, EEPROM, RAM, etc.), solid-state storage media (e.g., flash drive, etc.), and/or other electronically readable storage media. Electronic storage 130 may store software algorithms, information determined by processor 110, information received via user interface 120, and/or other information that enables system 10 to function properly. For example, electronic storage 130 may record or store vectors of parameters based on the generated output signals, and/or other parameters (as discussed elsewhere herein), and/or other information. Electronic storage 130 may be a separate component within system 10, or electronic storage 130 may be provided integrally with one or more other components of system 10 (e.g., processor 110).

User interface 120 of system 10 in FIG. 1 is configured to provide an interface between system 10 and a user (e.g., a user 108, subject 106, a caregiver, a therapy decision-maker, etc.) through which the user can provide information to and receive information from system 10. This enables data, results, and/or instructions and any other communicable items, collectively referred to as "information," to be communicated between the user and system 10. An example of information that may be conveyed by user 108 to system 10 is patient-specific adherence information. An example of information that may be conveyed to user 108 is a report detailing adherence information for subject 106. Examples of interface devices suitable for inclusion in user interface 120 include a keypad, buttons, switches, a keyboard, knobs, levers, a display screen, a touch screen, speakers, a microphone, an indicator light, an audible alarm, and a printer. Information may be provided to user 108 or subject 106 by user interface 120 in the form of auditory signals, visual signals, tactile signals, and/or other sensory signals.

It is to be understood that other communication techniques, either hard-wired or wireless, are also contemplated herein as user interface 120. For example, in one embodiment, user interface 120 may be integrated with a removable storage interface provided by electronic storage 130. In this example, information is loaded into system 10 from removable storage (e.g., a smart card, a flash drive, a removable disk, etc.) that enables the user(s) to customize system 10. Other exemplary input devices and techniques adapted for use with system 10 as user interface 120 include, but are not limited to, an RS-232 port, RF link, an IR link, modem (telephone, cable, Ethernet, internet or other). In short, any technique for communicating information with system 10 is contemplated as user interface 120.

Processor 110 of system 10 in FIG. 1 is configured to provide information processing capabilities in system 10. As such, processor 110 includes one or more of a digital processor, an analog processor, a digital circuit designed to process information, an analog circuit designed to process information, and/or other mechanisms for electronically processing information. Although processor 110 is shown in FIG. 1 as a single entity, this is for illustrative purposes only. In some embodiments, processor 110 includes a plurality of processing units.

As is shown in FIG. 1, processor 110 is configured to execute one or more computer program modules. The one or more computer program modules include one or more of parameter determination module 111, control module 112, characterization module 113, and/or other modules. Processor 110 may be configured to execute modules 111-113 by software; hardware; firmware; some combination of software, hardware, and/or firmware; and/or other mechanisms for configuring processing capabilities on processor 110.

It should be appreciated that although modules 111-113 are illustrated in FIG. 1 as being co-located within a single processing unit, in embodiments in which processor 110 includes multiple processing units, one or more of modules 111-113 may be located remotely from the other modules. The description of the functionality provided by the different modules 111-113 described herein is for illustrative purposes, and is not intended to be limiting, as any of modules 111-113 may provide more or less functionality than is described. For example, one or more of modules 111-113 may be eliminated, and some or all of its functionality may be incorporated, shared, integrated into, and/or otherwise provided by other ones of modules 111-113. Note that processor 110 may be configured to execute one or more additional modules that may perform some or all of the functionality attributed below to one of modules 111-113.

Parameter determination module 111 of system 10 in FIG. 1 is configured to determine one or more parameters from output signals generated by sensor(s) 142. The one or more parameters may include a first parameter, and/or other parameters. The first parameter may indicate (magnitude of) energy amplitude, e.g. in a first frequency band. For example, the first parameter may indicate the amplitude of the ultrasonic energy received by microphone 142 as described elsewhere herein. In some embodiments, parameter determination module 111 is configured to determine additional (spectral) parameters in a manner similar to the first parameter, though, e.g., corresponding to other frequency bands.

Operation of parameter determination module 111 may be performed in an ongoing manner, for example at a particular sampling rate. The one or more parameters may be determined at different locations and/or positions within system 10 or near subject 106. In some embodiments, parameter determination module 111 may derive vectors of parameters in an ongoing manner during a period of monitoring subject 106. The vectors of the parameters may be based on vectors of generated output signals and/or other (vectors of) determined parameters.

Characterization module 113 is configured to determine one or more characterizations of ultrasonic energy emitted by one or more of respiratory therapy delivery device 11a, respiratory medicament delivery device 11, and/or (the airway of) subject 106. The one or more characterizations may be based on one or more parameters determined by parameter determination module 111. In some implementations, characterization module 113 may be configured to determine a characterization of the ultrasonic energy emitted by a piezoelectric element having a particular operating frequency and/or emitted by subject 106. For example, the characterization may include whether ultrasonic energy emitted by the airway of subject 106 during inhalation is present.

Control module 112 is configured to control respiratory therapy delivery device 11a during operation. Operation of control module 112 may be based on one or more parameters determined by parameter determination module 111 and/or one or more characterizations determined by characterization module 113. Control by control module 112 may include adjustments, e.g. of the operating frequency, drive power, and/or any other adjustable operating conditions as described herein. Adjustments may be based on determined (spectral) parameters and/or generated output signals. Adjustments may be made such that a particular determined parameter, e.g. the first parameter described above, is maintained at or above at or above a predetermined threshold level. In some implementations, such a threshold is predetermined at a percentage of the known maximum for the particular determined parameter. The predetermined percentage may be about 80%, about 90%, about 95%, about 97%, about 98%, about 99%, and/or another percentage. Adjustments may be made in an ongoing manner, for example at a particular sampling rate. Adjustments may be made in real-time or near-real-time. The rate of adjustment may be milliseconds, 0.5 second, 1 second, 2 seconds, 5 seconds, 10 seconds, 20 seconds, and/or another appropriate rate. In some implementations, adjustments may be made responsive to a characterization (by characterization module 113) that ultrasonic energy is being emitted by the airway of subject 106 during inhalation. In some implementations, adjustments may be made in response (or caused by) a transition of a phase-locked loop circuit from unlocked to locked, for example phase-locked loop circuit 1203 as depicted in FIG. 12. Using other characteristics and/or transitions of the phase-locked loop circuit is envisioned within the scope of this disclosure.

In some implementations, parameter determination module 111 may be configured to determine an adherence metric and/or an adherence parameter for subject 106. The adherence metric and/or adherence parameter may be based on one or more previously described parameters and/or characterizations. For example, a particular adherence metric may be based on a combination of device actuation information and respiratory timing. An adherence metric and/or adherence parameter may for example be expressed as a percentage of perfect compliance with the recommended treatment. For example, if a particular patient scored a 90% adherence, such a score that may be considered by a care giver in determining a course of action. Alternatively, if a particular patient scored a low percentage of adherence, such a score may be considered relevant before the particular drug is deemed ineffective for that particular patient. Low scores may prompt a change in the chosen type of respiratory device.

Figure 2:
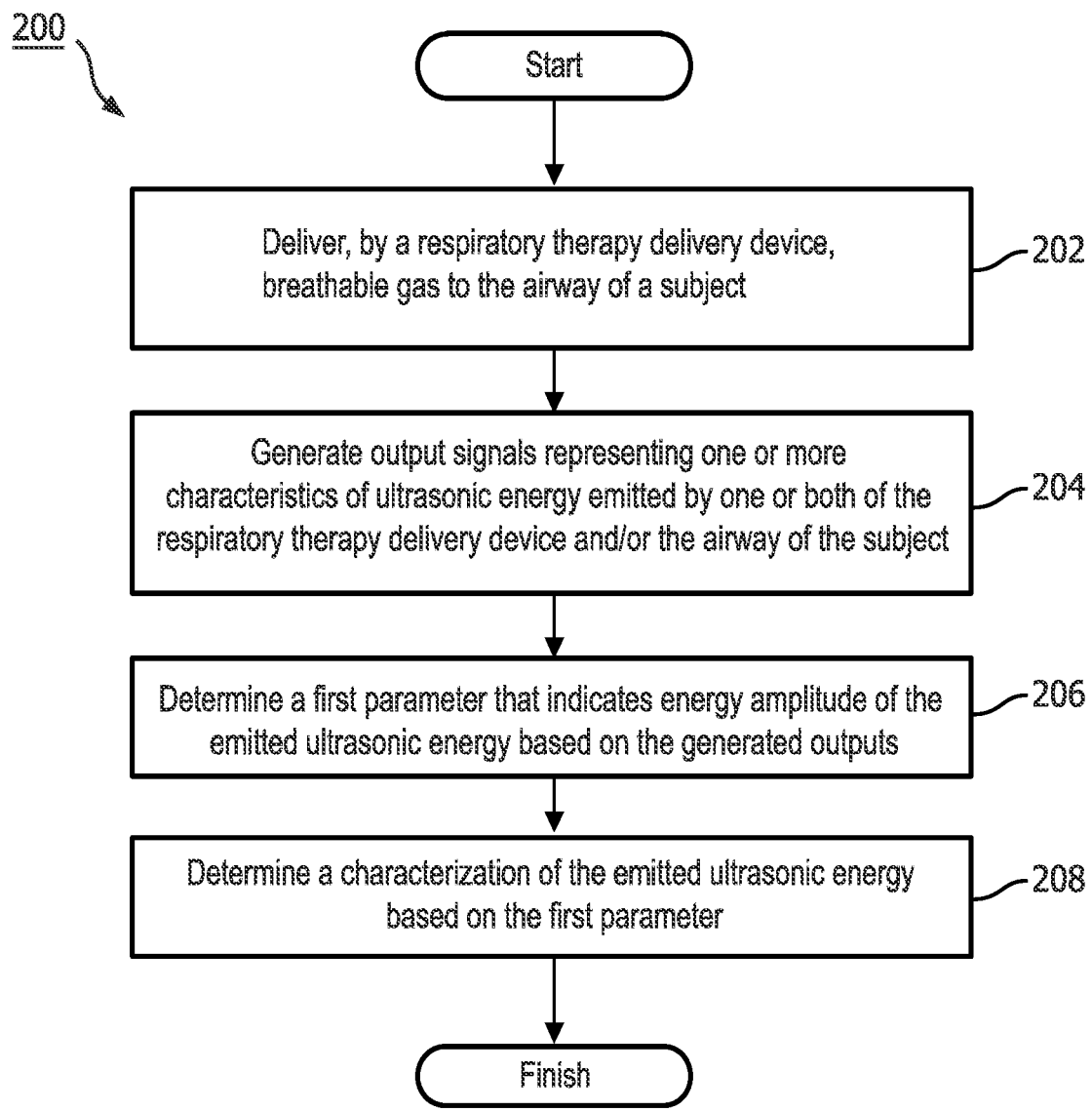
FIG. 2 illustrates a method of delivering respiratory therapy to a subject.

FIG. 2 illustrates a method 200 to deliver respiratory therapy to a subject, including but not limited to delivery of medicament. The operations of method 200 presented below are intended to be illustrative. In certain embodiments, method 200 may be accomplished with one or more additional operations not described, and/or without one or more of the operations discussed. Additionally, the order in which the operations of method 200 are illustrated in FIG. 2 and described below is not intended to be limiting.

In certain embodiments, method 200 may be implemented in one or more processing devices (e.g., a digital processor, an analog processor, a digital circuit designed to process information, an analog circuit designed to process information, and/or other mechanisms for electronically processing information). The one or more processing devices may include one or more devices executing some or all of the operations of method 200 in response to instructions stored electronically on an electronic storage medium. The one or more processing devices may include one or more devices configured through hardware, firmware, and/or software to be specifically designed for execution of one or more of the operations of method 200.

At an operation 202, breathable gas is delivered, by a respiratory therapy delivery device, to an airway of a subject. In some embodiments, operation 202 is performed by a respiratory therapy delivery device the same as or similar to respiratory therapy delivery device 11a and/or respiratory medicament delivery device 11 (both shown in FIG. 1 and described herein).

At an operation 204, output signals are generated that represent one or more characteristics of the ultrasonic energy emitted by one or both of the respiratory therapy delivery device and/or the airway of the subject. In some embodiments, operation 204 is performed by a sensor the same as or similar to sensor 142 (shown in FIG. 1 and described herein, also referred to as microphone 142).

At an operation 206, a first parameter is determined that indicates energy amplitude of emitted ultrasonic energy. The ultrasonic energy is emitted in a first ultrasonic frequency range. The first parameter is based on generated output signals. In some embodiments, operation 206 is performed by a parameter determination module the same or similar to parameter determination module 111 (shown in FIG. 1 and described herein).

At an operation 208, a characterization is determined of the emitted ultrasonic energy. The characterization is based on the first parameter. In some embodiments, operation 208 is performed by a characterization module the same as or similar to characterization module 113 (shown in FIG. 1 and described herein).

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although this description includes details for the purpose of illustration based on what is currently considered to be the most practical and preferred embodiments, it is to be understood that such detail is solely for that purpose and that the disclosure is not limited to the disclosed embodiments, but, on the contrary, is intended to cover modifications and equivalent arrangements that are within the spirit and scope of the appended claims. For example, it is to be understood that, to the extent possible, one or more features of any embodiment are contemplated to be combined with one or more features of any other embodiment.

The invention claimed is:

1. A system configured to provide respiratory therapy to a subject, the system comprising:
   a respiratory therapy delivery device configured to deliver breathable gas to an airway of a subject during inhalation;
   an ultrasonic sensor for detecting ultrasonic energy, the ultrasonic sensor configured to generate output signals conveying information related to ultrasonic energy emitted by the airway of the subject; and
   one or more processors configured to execute computer program modules, the computer program modules comprising:
      a parameter determination module configured to determine, based on the generated output signals, a first parameter that indicates energy amplitude of the emitted ultrasonic energy; and
      a characterization module configured to determine a characterization of the emitted ultrasonic energy, wherein the characterization is based on the first parameter, and wherein the characterization includes one or more respiratory parameters of the subject.

2. The system of claim 1, wherein the respiratory therapy delivery device includes a piezoelectric element and a conduit configured to fluidly couple the piezoelectric element and a subject interface appliance, wherein the characterization determined by the characterization module includes a detection of one or more changes in temperature and/or humidity within the conduit caused by respiratory actuation of the subject, wherein the computer control programs further comprise:
   a control module configured to control the respiratory therapy delivery device during operation through an adjustment of the piezoelectric element responsive to the characterization that temperature and/or humidity within the conduit has changed.

3. The system of claim 1, wherein the ultrasonic sensor comprises a microphone.

4. The system of claim 1, wherein the respiratory therapy delivery device includes a piezoelectric element, the piezoelectric element having an operating frequency during operation, wherein the sensor is configured to generate output signals conveying information related to one or more characteristics of ultrasonic energy emitted from the airway of the subject during inhalation, wherein the characterization determined by the characterization module includes whether ultrasonic energy emitted by the airway of the subject during inhalation is present, and wherein the computer program modules further comprise:

a control module configured to control the respiratory therapy delivery device during operation through an adjustment of one or both of the operating frequency of the piezoelectric element and/or an operation power level responsive to the characterization that ultrasonic energy is being emitted by the airway of the subject during inhalation.

5. The system of claim 4, wherein the respiratory therapy delivery device includes a phase locked loop circuit configured to control the piezoelectric element, wherein the sensor is further configured to generate output signals conveying information related to one or more characteristics of ultrasonic energy emitted by the piezoelectric element, and wherein the adjustment of one or both of the operating frequency of the piezoelectric element and/or an operation power level is caused by a transition of the phase locked loop circuit from unlocked to locked.

6. A method of providing respiratory therapy to a subject, the method comprising;

delivering, by a respiratory therapy delivery device, breathable gas to an airway of a subject during inhalation;

generating, by an ultrasonic sensor, output signals representing one or more characteristics of the ultrasonic energy emitted by the airway of the subject;

determining a first parameter that indicates energy amplitude of the emitted ultrasonic energy based on the generated output signals; and determining a characterization of the emitted ultrasonic energy, wherein the characterization is based on the first parameter, and wherein determining the characterization includes determining one or more respiratory parameters of the subject.

7. The method of claim 6, wherein the respiratory therapy delivery device includes a piezoelectric element and a conduit, wherein determining the characterization of the emitted ultrasonic energy includes detecting one or more changes in temperature and/or humidity within the conduit caused by respiratory actuation of the subject, the method further comprising:

fluidly coupling, by the conduit, the piezoelectric element and a subject interface appliance; and controlling the respiratory therapy delivery device during operation through an adjustment of the piezoelectric element, wherein controlling the respiratory therapy delivery device is responsive to detecting that temperature and/or humidity within the conduit has changed.

8. The method of claim 6, wherein the respiratory therapy delivery device includes a piezoelectric element, the piezoelectric element having an operating frequency during operation, wherein the generated output signals convey information related to one or more characteristics of ultrasonic energy emitted from the airway of the subject during inhalation, wherein the characterization includes whether ultrasonic energy emitted by the airway of the subject during inhalation is present, the method further comprising:

controlling the respiratory therapy delivery device during operation through an adjustment of one or both of the operating frequency of the piezoelectric element and/or an operation power level, wherein controlling the respiratory therapy delivery device is responsive to the characterization that ultrasonic energy is being emitted by the airway of the subject during inhalation.

9. The method of claim 8, wherein the generated output signals convey information related to one or more characteristics of ultrasonic energy emitted by the piezoelectric element, wherein the respiratory therapy delivery device includes a phase locked loop circuit, wherein the adjustment of one or both of the operating frequency of the piezoelectric element and/or an operation power level is caused by a transition of the phase locked loop circuit from unlocked to locked.

\* \* \* \* \*